(12) United States Patent
Perry et al.

(10) Patent No.: US 11,015,014 B2
(45) Date of Patent: May 25, 2021

(54) AUTOMATED CONTACTLESS ACCESS DEVICE LOCATION SYSTEM AND METHOD

(71) Applicant: Visa International Service Association, San Francisco, CA (US)

(72) Inventors: George Perry, Oakland, CA (US); Penny Jurss, Delafield, WI (US)

(73) Assignee: VISA INTERNATIONAL SERVICE ASSOCIATION, San Francisco, CA (US)

( * ) Notice: Subject to any disclaimer, the term of this patent is extended or adjusted under 35 U.S.C. 154(b) by 142 days.

(21) Appl. No.: 16/277,755

(22) Filed: Feb. 15, 2019

(65) Prior Publication Data

US 2019/0218332 A1 Jul. 18, 2019

Related U.S. Application Data

(60) Division of application No. 14/809,889, filed on Jul. 27, 2015, now Pat. No. 10,269,014, which is a
(Continued)

(51) Int. Cl.
| | |
|---|---|
| *G06Q 20/40* | (2012.01) |
| *C08G 18/48* | (2006.01) |
| *G06Q 20/34* | (2012.01) |
| *G06Q 20/32* | (2012.01) |
| *G06F 16/28* | (2019.01) |

(Continued)

(52) U.S. Cl.
CPC .......... *C08G 18/4887* (2013.01); *C07C 67/12* (2013.01); *C07C 67/26* (2013.01); *C08G 18/14* (2013.01); *C08G 18/36* (2013.01); *C08G 18/4288* (2013.01); *C08G 18/72* (2013.01); *G06F 16/285* (2019.01); *G06Q 20/3224* (2013.01); *G06Q 20/3278* (2013.01);
(Continued)

(58) Field of Classification Search
None
See application file for complete search history.

(56) References Cited

U.S. PATENT DOCUMENTS

| | | |
|---|---|---|
| 6,883,708 B1 | 4/2005 | Fiedler et al. |
| 8,265,864 B1 | 9/2012 | Kaurman et al. |
| | (Continued) | |

FOREIGN PATENT DOCUMENTS

| | | |
|---|---|---|
| KR | 10-2008-0023407 A | 3/2008 |
| KR | 10-2011-0113375 A | 10/2011 |

OTHER PUBLICATIONS

International Search Report and Written Opinion dated May 27, 2013 in PCT/US2013/024992, 11 pages.

*Primary Examiner* — Ajit Patel
(74) *Attorney, Agent, or Firm* — Kilpatrick Townsend & Stockton LLP

(57) ABSTRACT

A method is disclosed. The method includes receiving transaction data in an authorization request message from an access device, where the transaction data is associated with a merchant and a transaction location. The method also includes analyzing the transaction data to determine if a location database comprises location data corresponding to the merchant associated with the transaction data, and adding the transaction location and information regarding the access device to the location database.

20 Claims, 28 Drawing Sheets

Related U.S. Application Data continuation of application No. 13/761,032, filed on Feb. 6, 2013, now Pat. No. 9,129,281.

(60) Provisional application No. 61/595,448, filed on Feb. 6, 2012.

(51) Int. Cl.

| | | |
|---|---|---|
| *C07C 67/12* | (2006.01) | |
| *C07C 67/26* | (2006.01) | |
| *C08G 18/08* | (2006.01) | |
| *C08G 18/36* | (2006.01) | |
| *C08G 18/42* | (2006.01) | |
| *C08G 18/72* | (2006.01) | |
| *C08G 101/00* | (2006.01) | |

(52) U.S. Cl.
CPC ........... *G06Q 20/352* (2013.01); *G06Q 20/40* (2013.01); *G06Q 20/4016* (2013.01); *C08G 2101/00* (2013.01)

(56) References Cited

U.S. PATENT DOCUMENTS

| | | | |
|---|---|---|---|
| 2007/0055785 A1* | 3/2007 | Stevens | G06Q 20/405 709/229 |
| 2008/0222038 A1* | 9/2008 | Eden | G06Q 20/20 705/44 |
| 2010/0036741 A1 | 2/2010 | Cleven | |
| 2010/0061294 A1* | 3/2010 | Proctor, Jr. | G06Q 30/0261 370/328 |
| 2010/0082454 A1 | 4/2010 | Narayanaswami et al. | |
| 2010/0216396 A1 | 8/2010 | Fernandez | |
| 2011/0191161 A1 | 8/2011 | Dai | |
| 2011/0238510 A1* | 9/2011 | Rowen | G06K 9/3283 705/16 |
| 2011/0264586 A1 | 10/2011 | Boone et al. | |
| 2012/0123935 A1 | 5/2012 | Brudnicki et al. | |
| 2012/0197691 A1 | 8/2012 | Grigg | |
| 2012/0265685 A1 | 10/2012 | Brudnicki | |
| 2012/0310760 A1 | 12/2012 | Phillips | |
| 2013/0046635 A1 | 2/2013 | Grigg et al. | |
| 2013/0138521 A1 | 5/2013 | Want et al. | |
| 2013/0166398 A1 | 6/2013 | Minde | |

\* cited by examiner

AUTOMATED CONTACTLESS ACCESS DEVICE LOCATION SYSTEM AND METHOD

CROSS-REFERENCES TO RELATED APPLICATIONS

The present application is a divisional of U.S. patent application Ser. No. 14/809,889, filed Jul. 27, 2015, which is a continuation of U.S. patent application Ser. No. 13/761,032 filed Feb. 6, 2013, now U.S. Pat. No. 9,129,281, which is a non-provisional application of and claims priority to U.S. Provisional Application No. 61/595,448, filed on Feb. 6, 2012, the entire contents of which are all herein incorporated by reference for all purposes.

BACKGROUND

When conducting financial transactions, it has become increasingly common that a consumer may present a portable consumer device (such as a credit card) that has the ability to communicate with a merchant's point-of-sale (POS) terminal or other access device using some form of contactless communication. This may eliminate the need for traditional swiping of the payment device, and also enables the use of alternate payment devices (such as virtual wallets on mobile phones).

Until adoption of contactless access devices by merchants and other institutions becomes more common, consumers may have a difficult time determining where contactless payment devices are accepted. This may force customers to carry both traditional and contactless payment methods, thus reducing the potential benefits of using contactless payment devices.

It is also difficult to determine where contactless access devices are located. Many merchants may install contactless access devices (e.g., contactless POS terminals), but many consumers may not know that those merchants have installed contactless access devices and are willing to accept contactless payment devices. Those merchants may consequently lose business. Traditional methods for determining the locations of contactless access devices include using human beings to go and personally visit merchants and record where these access devices would be used. This is inefficient.

It would be desirable to provide for a more efficient way to determine the location of a contactless access device. It would also be desirable to provide consumers with better ways to determine which merchants or locations might accept contactless payment devices.

Embodiments of the invention address these and other problems.

SUMMARY

Embodiments of the invention provide for improvements in locating contactless access devices and storing those locations in a database. The database can be accessed by consumers to find the locations of such access devices. In other embodiments, individuals can access the database to perform determine where such contactless access devices are used for analytics and the like.

Embodiments of the invention allow issuers to add location data corresponding to contactless access devices to a location database. Issuers may also define custom mapping parameters to be added to a mapping database. The mapping parameters may be used to determine map data sent to consumers associated with issuers.

Embodiments of the invention also enable a server computer in a payment processing network, or other system, to retrieve location data from transactions and add the transaction location data to the location database. A location server computer uses the location database and the mapping database to electronically transmit map data to a software application. The software application may use the map data to generate a map showing nearby contactless access devices, allow a user to filter the depicted contactless access devices on the map, display information about the contactless access devices, and perform actions relating to the contactless access devices.

One embodiment of the invention is directed to a computer-implemented method comprising receiving mapping parameters, wherein the mapping parameters provide parameters for generating a map, receiving location data corresponding to contactless access devices, and adding, to a location database, the location data corresponding to the contactless access devices. The method also comprises adding, to a mapping database, the mapping parameters. Another related embodiment can be directed to server computer comprising a processor and a non-transitory computer readable medium. The computer-readable storage medium comprises code executable by the processor for performing the method.

Another embodiment of the invention is directed to a method comprising receiving transaction data in an authorization request message from an access device, wherein the transaction data is associated with a merchant and a transaction location. The method also comprises analyzing the transaction data to determine if a location database comprises location data corresponding to the merchant associated with the transaction data, and adding the transaction location and information regarding the access device to the location database. Another related embodiment can be directed to server computer comprising a processor and a non-transitory computer readable medium. The computer-readable storage medium comprises code executable by the processor for performing the method.

Another embodiment of the invention is directed to a method comprising transmitting, by a software application running on a computing device, a location associated with the computing device, and receiving map data from a location server. The map data is operable by the software application to cause the computing device to: display a map, wherein locations of contactless access devices nearby to the location associated with the computing device are shown, filter for contactless access devices, wherein one or more of the nearby contactless access devices may be hidden from the map based on a filter, and display information associated with a contactless access device.

Further details regarding embodiments of the invention can be found in the Detailed Description and the Figures.

DETAILED DESCRIPTION

Figure 1:
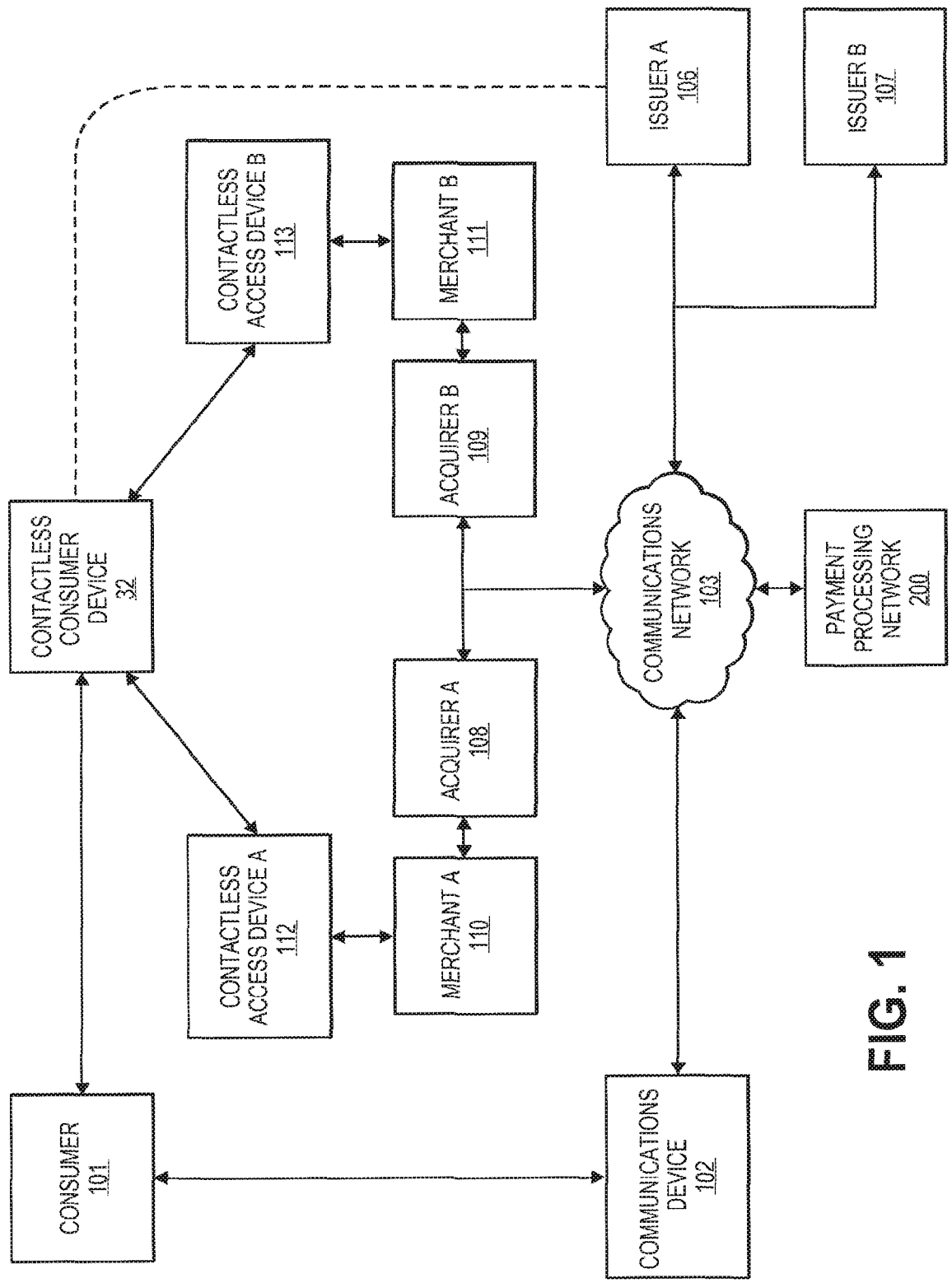
FIG. 1 shows a block diagram of a system according to an embodiment of the invention illustrating the relationship between various entities which may interact with a payment processing network.

Prior to discussing embodiments of the invention, description of some terms may be helpful in understanding embodiments of the invention.

A "server computer" may include a powerful computer or cluster of computers. For example, the server computer can be a large mainframe, a minicomputer cluster, or a group of servers functioning as a unit. In one example, the server computer may be a database server coupled to a Web server. The server computer may be coupled to a database and may include any hardware, software, other logic, or combination of the preceding for servicing the requests from one or more client computers. The server computer may comprise one or more computational apparatuses and may use any of a variety of computing structures, arrangements, and compilations for servicing the requests from one or more client computers.

An "access device" may refer to any suitable device for communicating with merchant and for interacting with a portable consumer device. An access device can be in any suitable location such as at the same location as a merchant. An access device may be in any suitable form. Some examples of access devices include POS terminals, cellular phones, PDAs, personal computers (PCs), tablet PCs, handheld specialized readers, set-top boxes, electronic cash registers (ECRs), automated teller machines (ATMs), virtual cash registers (VCRs), kiosks, security systems, access systems, Websites, and the like. Typically, an access device may use any suitable contact or contactless mode of operation to electronically transmit or receive data from a portable consumer device.

A "contactless access device" may refer to an access device that may communicate using short range wireless communications. This may comprise any method of providing short-range wireless communications capability, such as RFID, Bluetooth™, infra-red, or other data transfer capability that can be used to exchange data between a portable consumer device and an access device. In some embodiments, short range wireless communications may be in conformance with a standardized protocol or data transfer mechanism (e.g., ISO 14443/NFC). Short range wireless communication in financial transactions typically comprises communications at a range of less than 2 meters (but preferably over much shorter distances).

A "communications channel" may include any suitable path for communication between two or more entities. Suitable communications channels may be present directly between two entities such as a client computer and a gateway server, or may include a number of different entities. Any suitable communications protocols may be used for communications channels according to embodiments of the invention.

A "communications device" may include any suitable device operable to communicate over a wired or wireless computer network. Examples of communications devices may include server computers, desktop computers, laptop computers, tablets, mobile phones, or microcomputers.

"Electronically" (as in, for example, electronically receiving, storing, transmitting, sending, etc.) may comprise any suitable manner of transferring, utilizing, receiving, any information or data that is in electronic form. For example, this may comprise utilizing a network (such as the Internet, a wireless network, or LAN), but is not so limited. As another example, "electronically" may include optical transmission/reception, radio frequency transmission/reception, or any other manner of transmitting, receiving, storing, or processing data in electronic form.

"Geo-location" may refer to the physical location of an object in the world. This may be described in any suitable manner, such as by longitude and latitude coordinates, or by a more identifiable venue such as a city or street address or point of interest (or proximity thereto).

A "contactless consumer device" or "contactless payment device" may refer to any suitable device that allows a transaction to be conducted with a merchant using short-range wireless communications. A contactless consumer device may be in any suitable form. For example, suitable contactless consumer devices can be hand-held and compact so that they can fit into a consumer's wallet and/or pocket (e.g., pocket-sized). They may include smart cards, magnetic stripe cards, keychain devices (such as the Speedpass™ commercially available from Exxon-Mobil Corp.), Visa payWave™ devices, etc. Other examples of portable consumer devices include cellular phones, personal digital assistants (PDAs), pagers, contactless payment cards, security cards, access cards, smart media, transponders, and the like.

"Location data" may refer to any data associated with a location of a contactless access device. Location data may relate to information regarding a physical location of an access device, or can include data that provides a location for an access device. Examples of location data may include a location name corresponding to a contactless access device, location geo-data or geo-location for an access device or merchant that uses access devices, access device properties associated with the location, a location image URL, a location icon URL, a location description, etc.

The term "mapping parameter" may refer to any parameter or indication which may be used to influence the manipulation of map data to display a map. Examples of mapping parameters may include an issuer identifier, an issuer group service provider identifier, pre-populated location data identifiers, location type filters, merchant acquirer filters, contactless access device filters, etc.

"Map data" may include any data used to display a map, or any data that can be provided in conjunction with a map. The map may be a map of contactless access devices. Map data may also comprise properties of the contactless access devices, such as the make and model of the devices, and technologies supported by the devices. Map data may also comprise information regarding the a merchant, bank, ATM, or other institution associated with contactless access devices, such as addresses, phone numbers, customer ratings, hours of operation, and issuers and acquirers associated with the institutions.

Embodiments of the invention provide for many technical advantages. For example, embodiments of the invention allow users of contactless payment devices to quickly and conveniently determine nearby merchants, financial institutions, and other institutions with contactless access devices that support contactless transactions. The user may also filter the contactless access devices, so that only devices with specific characteristics are shown. By allowing the user to easily determine the geo-locations of nearby contactless access devices, the user may be further encouraged to adopt contactless consumer devices.

Embodiments of the invention also provide the advantage of enabling merchants and financial institutions to advertise their support for contactless transactions. In embodiments of the invention, only merchants and financial institutions with contactless access devices may be displayed on a map viewed by users. Thus, merchants or financial institutions supporting contactless technology and entered into a location database would be viewable by an additional group of users, namely those searching for support for contactless transactions.

Embodiments of the invention provide the further advantage of combining records of contactless access devices that may have previously been stored in multiple independent databases. Embodiments of the invention disclose a method for adding location data associated with an issuer to a location database for contactless access devices. Providing a single location database allows users to query the database for all contactless access devices nearby to a location. This allows users of the location database to quickly and conveniently determine all contactless access devices nearby a location, without having to search multiple databases.

In addition, embodiments of the invention provide the technical advantage of generating location data from transaction data. Generating location data from transaction data addresses a problem with maintaining a location database, namely how location data is added to the database and kept up to date. Transaction data provides a useful source of location data of an access device. When contactless access devices are used for payment transactions, they may generate authorization request messages that may be transmitted to a payment processing network. In some embodiments of the invention, such as when the location database may be managed by a payment processing network, the payment processing network may analyze these messages to determine whether the transaction involved contactless payment. If so, in some embodiments of the invention, the corresponding location data may be added or updated in the location database. This allows the location database to be maintained with greatly reduced human effort in comparison to manually accounting for each contactless access device. In addition, such methods can enable additional logic governing the presence of contactless access devices in the location database. For example, contactless access devices which have not generated an authorization request message for a transaction for a given period of time (e.g., 6 months) may be removed from the location database. This allows the location database to better reflect available and active contactless access devices. The database is updated in a very efficient manner in embodiments of the invention, since transaction messages (e.g., authorization request message) are used for both database updates as well as transaction processing. Additional communications regarding the contactless access devices are not required, and this also saves on communications bandwidth.

Embodiments of the invention provide for the technical advantage of allowing issuers to customize maps generated for the consumers associated with an issuer by defining a set of mapping parameters. Mapping parameters may allow an issuer to display information specifically relevant to consumers associated with the issuer. For example, in some embodiments, an issuer may only want to display contactless access devices that are compatible with a contactless technology used by the issuer. Thus, the issuer may define a mapping parameter for a filter to only display contactless access devices of certain makes or models which are known to be compatible with the contactless technology. In some embodiments, an issuer may only want to display ATMs or bank branches associated with the issuer. In such a case, the issuer may define a mapping parameter for a filter on contactless access devices not operated by the issuer. In general, mapping parameters allow a consumer to get the benefits of a centralized database, while allowing issuers the ability to tailor map data received by consumers to the specific preferences associated with the issuer.

The above examples highlight only a few of the advantages of embodiments of the invention.

I. Exemplary Systems

FIG. 1 shows a system according to an embodiment of the invention. The system comprises a consumer (or user) 101, who may operate a communications device 102 such as a mobile phone. The consumer 101 may also hold a contactless consumer device 32 issued by an issuer such as issuer A 106. The communications device 102 may communicate with a number of entities via a communications network 103. The communications network 103 may allow for communication between a number of other entities including a payment processing network 200, a plurality of acquirers 108, 109, and a plurality of issuers 106, 107. A plurality of merchants 110, 111 may be in communication with and associated with a plurality of acquirers 108, 109, which may be in communication with a plurality of contactless access devices 112, 113 associated with the merchants 110, 111. The contactless consumer device 32 may be used to interact with the contactless access devices 112, 113 to initiate payment transactions or the like.

As will be described in further detail below, the payment processing network 200 that may include a location server computer and a location database. The location server computer and the location database may be linked to the various entities in the system via the communications network 103. The communications network 103 may comprise any suitable network(s), such as the Internet or a mobile cellular network. This enables each of the entities to receive information from the location database (such as geo-location and/or descriptive information) as well as to potentially submit information to update the location database (e.g., a merchant may indicate the make and model of an access device that they are using; and the issuers may request reports and analysis relating to the contactless access devices in the location database, submit financial services location information, and/or provide information for creating custom mappings).

As used herein, an "issuer" may typically refer to a business entity (e.g., a bank) that maintains financial accounts for the consumer 101 and often issues a contactless consumer device 32 such as a credit or debit card to the consumer 101. A "merchant" is typically an entity that engages in transactions and can sell goods or services. An "acquirer" is typically a business entity (e.g., a commercial bank) that has a business relationship with a particular merchant or other entity. Some entities can perform both issuer and acquirer functions. Some embodiments may encompass such single entity issuer-acquirers. Each of the entities (e.g., merchants 110, 111 and issuers 106, 107 may comprise one or more computer apparatuses to enable communications through the communications network 103, or to perform one or more of the functions described herein.

The payment processing network 200 may include data processing subsystems, networks, and operations used to support and deliver certificate authority services, authorization services, exception file services, and clearing and settlement services. An exemplary payment processing network may include VisaNet™. Payment processing networks such as VisaNet™ are able to process credit card transactions, debit card transactions, and other types of commercial transactions. VisaNet™, in particular, includes a VIP system (Visa Integrated Payments system) which processes authorization requests and a Base II system which performs clearing and settlement services.

The payment processing network 200 may include a server computer. A server computer is typically a powerful computer or cluster of computers. For example, the server computer can be a large mainframe, a minicomputer cluster, or a group of servers functioning as a unit. In one example, the server computer may be a database server coupled to a Web server. The payment processing network 220 may use any suitable wired or wireless network, including the Internet. As noted above, in some embodiments, the location server computer and/or location database may be located at the payment processing network 220, or the payment processing network 220 may provide data to the location server computer and/or the location database.

In a typical purchase transaction, the consumer 101 purchases a good or service at merchant A 110 using contactless consumer device 32 such as an NFC-enabled phone. The user's contactless consumer device 32 can interact with a contactless access device A 112 at the merchant A 110. For example, the user may tap the contactless consumer device 32 against an NFC reader in the contactless access device A 112.

An authorization request message is generated by the contactless access device A 112 and is then forwarded to the acquirer A 108. After receiving the authorization request message, the authorization request message is then sent to the payment processing network 200. The payment processing network 200 then forwards the authorization request message to the corresponding issuer A 106 of the contactless consumer device 32.

An "authorization request message" may be an electronic message that is sent to a payment processing network and/or an issuer of a payment card to request authorization for a transaction. An authorization request message according to some embodiments may comply with ISO 8583, which is a standard for systems that exchange electronic transaction information associated with a payment made by a consumer using a payment device or payment account. The authorization request message may include an issuer account identifier that may be associated with a payment device or payment account. An authorization request message may also comprise additional data elements corresponding to "identification information" including, by way of example only: a service code, a CVV (card verification value), a dCVV (dynamic card verification value), an expiration date, etc. . . . . An authorization request message may also comprise "transaction information," such as any information associated with a current transaction, such as the transaction amount, merchant identifier, merchant location, etc., as well as any other information that may be utilized in determining whether to identify and/or authorize a transaction. The authorization request message may also include other information such as information that identifies the access device that generated the authorization request message, information about the location of the access device, etc.

After the issuer A 106 receives the authorization request message, the issuer A 106 sends an authorization response message back to the payment processing network 200 to indicate whether or not the current transaction is authorized (or not authorized). The payment processing network 200 then forwards the authorization response message back to the acquirer A 108. The acquirer A 108 then sends the response message back to the merchant A 110.

An "authorization response message" may be an electronic message reply to an authorization request message generated by an issuing financial institution or a payment processing network. The authorization response message may include, by way of example only, one or more of the following status indicators: Approval—transaction was approved; Decline—transaction was not approved; or Call Center—response pending more information, merchant must call the toll-free authorization phone number. The authorization response message may also include an authorization code, which may be a code that a credit card issuing bank returns in response to an authorization request message in an electronic message (either directly or through the payment processing network) to the merchant's access device (e.g. POS equipment) that indicates approval of the transaction. The code may serve as proof of authorization. As noted above, in some embodiments, a payment processing network may generate or forward the authorization response message to the merchant.

After the merchant A 110 receives the authorization response message, the contactless access device A 112 at the merchant 110 may then provide the authorization response message for the user. The response message may be displayed by the contactless access device A 112, or may be printed out on a receipt.

At the end of the day, a normal clearing and settlement process can be conducted by the payment processing network 200. A clearing process is a process of exchanging financial details between and acquirer and an issuer to facilitate posting to a user's payment account and reconciliation of the user's settlement position.

Figure 2:
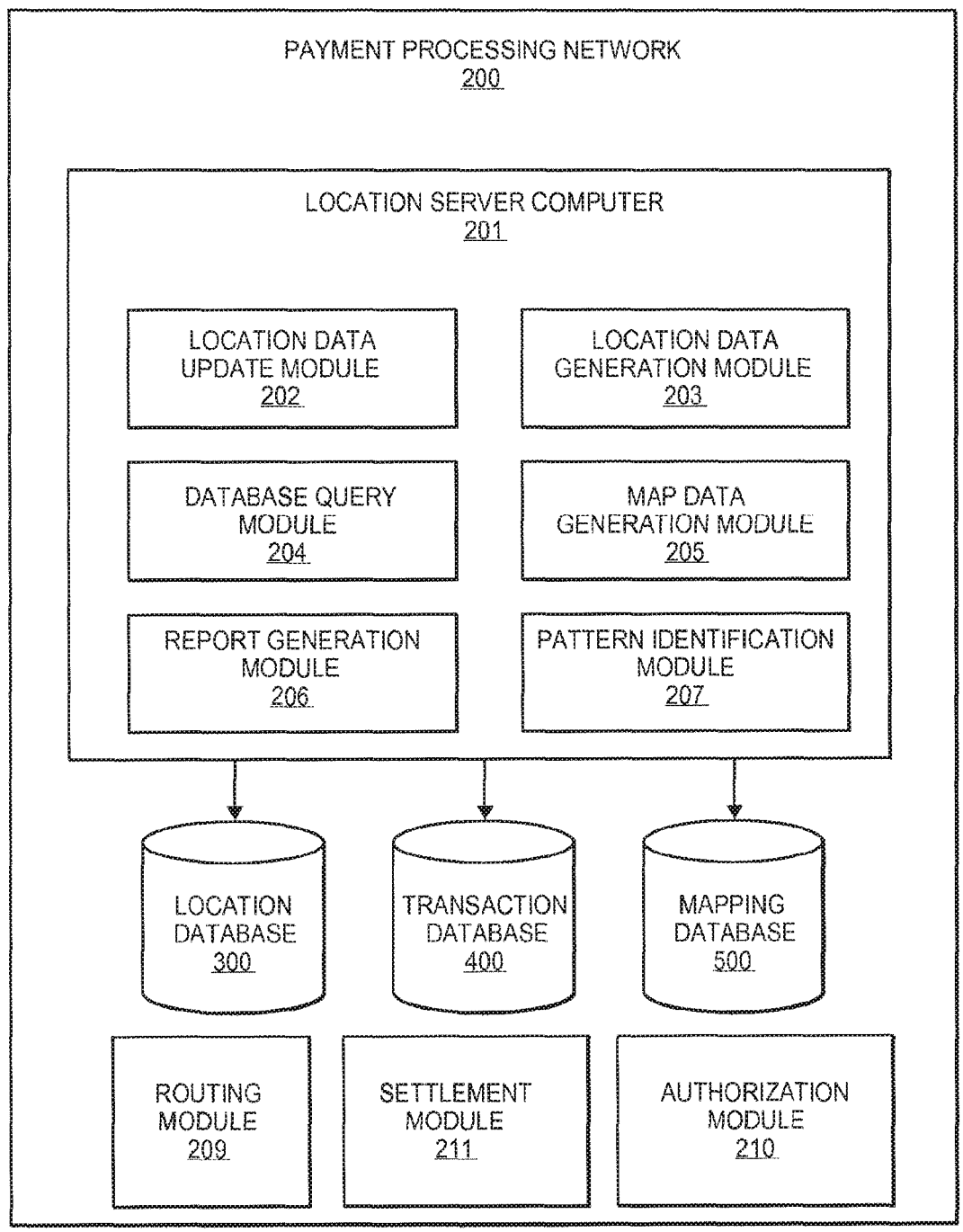
FIG. 2 shows a diagram of an exemplary payment processing network in one embodiment of the invention.

FIG. 2 illustrates some components in a payment processing network 200 according to an embodiment of the invention. The payment processing network 200 includes a routing module 220, a settlement module 230, and an authorization module 240. These modules may be included on computer readable media on one or more computers in the payment processing network 200.

The payment processing network 200 may also include a location server computer 201. The location server computer 201 may comprise, or be operatively coupled to, a location database 300, a transaction database 400, and a mapping database 500. The location database 300 may comprise the most up-to-date geo-location and other descriptive information regarding contactless wireless access devices, or other financial service entity and provider information. The transaction database 400 may comprise a set of transaction data previously received by the payment processing network 200. The mapping database 500 may comprise any information that is associated with the custom mapping provided for issuers or financial service providers, and may in some instances comprise one or more custom mapping parameters (or parameters for generating a custom map) such that the issuer's consumers may electronically receive map data based on the mapping database 500. The location server computer 201 may also comprise one or more software or hardware modules, including a location data update module 202, a location data generation module 203, a database query module 204, and a mapping generation module 205.

The location data update module 202 may be programmed or configured to maintain and update the location database 300, such in response to when new information about previous entries. The location data generation module 203 may be programmed or configured to generate data to be added to the location database 300, such as when location data is received about new entries, or to generate location data from transaction data stored in transaction database 400.

The database query module 204 may be configured or programmed to electronically send and receive commands from any databases in the payment processing network 200 (such as location database 300, transaction database 400, or mapping database 500) and to provide that information to the appropriate software or hardware module in location server computer 201. The database query module 204 may also be configured or programmed to electronically receive data requests sent by one of the entities in the system described in FIG. 1 and return any relevant data that was requested. The database query module 204 may also be utilized in conjunction with the report generation module 206 to provide relevant reports based on the data included in the location database 300 or mapping database 500.

The map data generation module 205 may be programmed or configured to perform some or all of the functions associated with generating custom mappings, including electronically receiving and identifying the parameters for the non-issuer contactless access devices to include, as well as the generation of the listing of the contactless access devices and/or using mapping parameters stored in the mapping database 500. An exemplary mapping process is later described with reference to FIGS. 25 and 26.

The pattern identification module 207 may work in conjunction with the report generation module 206 in generating reports based on the data included in the location database 300 or mapping database 500. In addition, the pattern identification module 207 also may search the location database 300 using any of the categories of information stored therein (e.g., geo-location information, merchant type, etc.) and identify patterns, trends, coverage, and/or marketing and/or promotional opportunities based on the data.

II. Exemplary Location Database Embodiments

Figure 3:
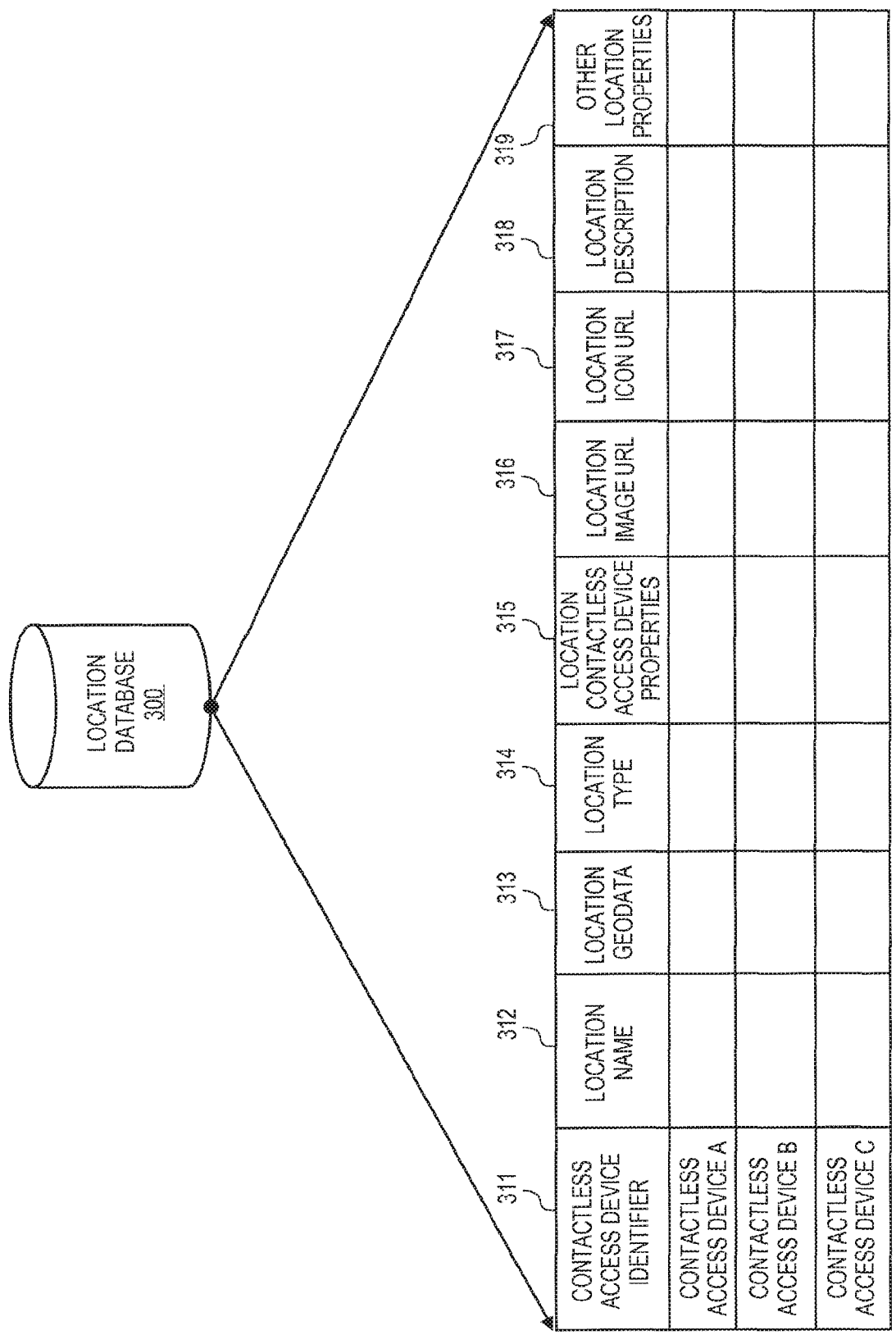
FIG. 3 shows a diagram of an exemplary location database in one embodiment of the invention.

With reference to FIG. 3, a more detailed illustration of an exemplary embodiment of a location database 300 is shown. The location database 300 may be configured to store some or all location data associated with various contactless access devices. Some possible categories of location data that may be stored in the database are described below. The location database 300 may comprise more than one database, and the databases may be in the same location or may be remotely located. Data stored in the location database 300 may include location data and/or data identifying a contactless access device. For example, the location database may comprise a contactless device identifier 311, location name 312, location geodata 313 (e.g., longitude and latitude coordinates), location type 314, location contactless access device properties 315, location image URL 316, location icon URL 317, location description 318, and other location properties 319.

The contactless device identifier 311 may be a unique identifier associated with a contactless device. The contactless device identifier 311 may be assigned by a manufacturer of the contactless access device, an acquirer associated with the contactless access device, the payment processing network, or any other party.

The location name 312 may be the name or other identifier of a location containing the contactless access device. For example, in some embodiments, the location name may be a merchant name if the contactless access device is operated by a merchant. Alternately, the location name may be a bank name if the contactless access device is operated by a bank.

The location geodata 312 may include a latitude and longitude pair, an address, city, state, postal code (such as a ZIP™ code), country, or any other information suitable to identify the location of the contactless access device. In some embodiments of the invention, if the contactless access device is operated within a merchant or bank, the geodata for the merchant or bank may be provided.

The location type 314 may indicate a category or other classifier for a type of location associated with the contactless access device. For example, in some embodiments, the merchant type may include a Merchant Category Code (MCC) for a merchant associated with the contactless access device. In some embodiments, Location type 314 may also be used to identify whether the location corresponds to a bank branch, ATM, or merchant.

The location contactless access device properties 315 may indicate properties of the contactless access device(s) at the location. For example, location contactless access device properties 315 may include the manufacturer of the contactless access device (i.e., the make) and/or a model associated with the manufacturer. In some embodiments of the invention, location contactless access device properties 315 may be used to provide an indication of protocols, technologies, payment products, or brands supported by the contactless access device. For example, an indication of whether the access device supports Bluetooth™, NFC, payWave™, or other technology may be included.

Location data may also comprise a location image URL 316 and location icon URL 317. In some embodiments, location image URL 316 and location icon URL 317 may be used to retrieve and display in an application or web page an image or icon associated the location corresponding to access device. Location image URL 316 and location icon URL 317 may refer to images or icons of any suitable format, such as GIF, JPEG, SWF, TIFF, or any other image format known in the art.

Location description 318 may be a text string describing a location associated with the contactless access device. Location description 318 may include information about the location provided by a third party, types of consumer devices accepted by at the location, or any other description of the location.

Other location properties 319 may include any properties associated with the location not previously mentioned. Examples of data that may be included in other location properties 319 include an acquirer associated with the contactless access device. The acquirer may be represented using an acquirer identifier.

In some embodiments, a date or time of last activity of the contactless access device and a phone number associated with the contactless access device may also be included in other location properties 319.

In some embodiments, a status of the contactless access device may be included in other location properties 319. The status of the contactless access device may represent information regarding the operational status of the contactless access device or information regarding how the device should be displayed on generated maps. For example, the status may indicate that the contactless access device should be displayed using a "coming soon" marker.

In some embodiments, a suppression flag may also be included in other location properties 319. The suppression flag may indicate that the device should not be displayed on generated maps, for example if the device is inactive or unready.

Contactless access devices may be added to the location database either through the use of lists or any other form of data supplied to a managing entity of the location database, or directly by the merchants, acquirers, issuers, etc. that operate or are associated with a contactless access device or other financial services locations. In some embodiments, such as when the database is imported from a third-party, location data may be imported in XML format. An exemplary table of XML tags that may be used in an XML schema is below:

| Field | Name | Type | Description | Comments |
|---|---|---|---|---|
| <store_id> | Store Name | Numeric | May correspond to location name 312 | Unique |
| <merchant> | Merchant Name | Alpha Numeric | May correspond to location name 312 | |
| <category_id> | Category Code | Numeric | May correspond to location type 314 | |
| <address1> | Street Address | Alpha Numeric | May correspond to location geodata 313 | |
| <city> | City Name | Alpha | | |
| <state> | State | Alpha | | |
| <zip> | Zip | Alpha Numeric | | |
| <country> | Country | Alpha | | |
| <latitude> | | Decimal | | |
| <longitude>- | | Decimal | | |
| <payment_products> | | Alpha | May correspond to location contactless access device properties 315 | |
| <phone_number> | | Alpha Numeric | May correspond to other location properties 319 | |
| <status> | | Numeric | | |
| <suppress> | | Numeric | | |

In other embodiments of the invention, such as when the location database may be managed by a payment processing network, transactional data may be analyzed to identify any contactless access devices and corresponding merchants that have recorded a contactless transaction, but for which have not yet been identified in the location database. In this manner, the location database may be kept up-to date as access devices are connected or disconnected from the system.

As noted above, the location database may provide contactless access device information to consumers, such as by linking to a website or a mobile device application. In some embodiments of the invention, an application programming interface (API) may be defined to enable access to the location database 300.

In one embodiment, the communication device 102 may generate a location data request message in JavaScript Object Notation (JSON) format. An example request message is shown below:

```
{"requestData" :
  {
    "address1" : metrocenter blvd,
    "city" : foster city,
    "State" :ca,
    "Latitude" : 7.790523,
    "Longitude" : 22.413101,
    "PaymentProductType" :PayWave,
    "NumberOfLocations" :50,
     "DistanceParameter" :3,
     "zipcode" :94040,
     "Country Code":US
  } ,
  "wsRequestHeaderV3" :
  {
    "requestTS" : "2008-09-19T00:00:00.000",
    "applicationID" : "BID",
    "requestMessageID" : "WS06-6010008",
    "correlationID" : "TEST",
    "userID" : "VPW_Test_6",
  }
}
```

In the shown embodiment, the request message is comprised of two Javascript object data structures, a "requestData" object, and a "wsRequestHeaderV3" object. The "address1", "city", "state", "Latitude", "Longitude", "zipcode", and "country Code" keys may be strings providing information regarding the current location of the consumer. The "paymentProductType" value may be a string providing information regarding a brand, technology, or protocol supported for the requested location data. For example, "paymentProductType" may have a value of "payWave" to indicate a request for Visa® payWave™ locations. The "NumberOfLocations" value indicates a number of locations requested. For example, if "NumberOfLocations" has the value of "5", the location data for the closest five satisfactory contactless access devices may be returned. The "DistanceParameter" value indicates that the requested contactless access devices should reside within the specified radius from the current location.

The "wsRequestHeaderV3" object generally comprises information relating to the location data request message itself. The "requestTS" value indicates a timestamp in Universal Coordinated Time (UTC) format. The "applicationID" value identifies the application used to generate the location data request message. In some embodiments of the invention, the "applicationID" value may be specific to an issuer or issuer group service provider. In such embodiments, the "applicationID" value may be used to determine which mapping parameters to use to process the location data request message. The "userID" value indicates a user or customer identifier. In some embodiments, the "userID" value may also be used to identify the mapping parameters to use to process the location data request message.

Once the location data request message is generated, it may be sent to the location server computer 201. Location server computer 201 may process the location data request message to generate map data. In one embodiment of the invention, the map data may be included in a JSON location data response message sent to the communication device 102. An example response message is shown below:

```
{"responseData":
[
    "storeID":123,
    "merchantName":gap,
    "categoryID":1,
    "address1":metrocenter blvd,
    "city":mountain view,
    "state":ca,
    "zip":94040,
    "country":USA,
    "paymentProductType":Giftcard,
    "phoneNumber":762342342,
    "latitude":345435345.24,
    "longitude":345345345.23,
    "status":1,
    "suppress":1
],...
"wsStatus":
  {
    "statusCode":"CDI000",
    "statusDesc":"Visa payWave Service - Success"
  },
  "wsResponseHeaderV2":
  {
    "responseTS":1331788708062,
    "requestMessageID":"WS06-6010008",
    "responseMessageID":"30MSP6130620120315051825755",
    "numOfRowsReturned":2
  }
}
```

In the shown embodiment, the location data response message is composed of three Javascript objects: a "responseData" object, a "wsStatus" object, and a "wsResponseHeaderV2" object.

The "responseData" object comprises an array of map data corresponding to one or more contactless access devices retrieved from location database 300. Typically, the array will have a length corresponding to the "numberOfLocations" value transmitted in the location data request message. The values for "merchantName" and "storeID" may correspond with location name 312 associated with the contactless access device in the location database 300. The "categoryID" key may correspond to the location type 314 stored in the location database 300. The "address1", "city", "state, "zip", "country", "latitude", and "longitude" values may correspond to location geodata 313 stored in the location database 300. The "paymentProductType" value may correspond to the location contactless access device properties 315. The "phoneNumber", "status", and "suppress" keys may correspond to other location properties 319 stored in the location database 300.

The "wsStatus" object indicates the status of the location data request. The "wsStatus" object may comprise a "statusCode" value and a "statusDesc" value. Typically, the "statusCode" is an alphanumeric code indicating of the status of the request, and the "statusDesc" message is a string description of the status.

The "wsResponseHeaderV2" object provides information regarding the response message itself. The object comprises a "responseTS" indicating a UTC timestamp of the response, a "requestMessageID" indicating an identifier of the corresponding location data request message, a "responseMessageID" indicating an identifier of the response message, and a "numRowsReturned" indicating the number of elements in the "responseData" array.

Typically, the communication device 102 may parse the location data response message to retrieve the map data.

In alternate embodiments, the information corresponding to location data may be maintained separately (e.g., the location data could be supplied to a web provider on a regularly scheduled basis, which information may then be used to populate the website (or a database coupled thereto). However, in some instances, the location database may be queried directly by consumers. This may enable consumers to identify contactless access devices and corresponding merchants, banks, and other institutions that accept payment devices having a particular contactless interface, and may further enable users to search for and filter for the type of data returned by using some of the information associated with a contactless access device (other than the geo-location information), such as the Merchant Category Codes assigned to the corresponding merchants.

In some embodiments, the consumer may be able to search for contactless access devices by manually entering in a zip code or address (e.g., entering data into a web browser or mobile device application) or the data could be generated automatically by an integrated location detector (e.g., a GPS program on a mobile device or through use of an IP address). The consumer's current location can then be compared against location data stored in the location database. In addition, the consumer may enter criteria other than geo-location information that may be searched against the location database entries (e.g., the user may specify information associated with other categories of data stored in the location database). Moreover, the consumer may receive information associated with the locations that may also be stored in the location database. Some examples of such information may include, but are not limited to, the location name, location address (and or geo-location data), location type, location image URL, icon URL, location description, location properties, services provided, telephone number, store hours, and whether there is handicap access on the premises.

In some embodiments, the database could include additional information, such as geo-location information for locations in which certain financial services may be provided. This could include, by way of example, locations in which pre-paid debit cards or gift cards may be obtained or reloaded, locations where financial products related to travel (e.g. electronic traveler's checks) may be obtained, or any other financial product or service is provided.

In some embodiments, system and methods may be provided that include a location database that may enable issuers and financial service providers to use a generic locator capability to upload branch, ATM, or any other location data they desire into the location database. This may enable customers with mobile devices to find nearby locations where financial services are provided by a particular issuer. Some examples of the types of location data issuers (or any other entity) may upload to the location database may include, but is not limited to: ATM locations, branch locations, merchant locations, prepaid payment device reload locations, and prepaid payment device purchase locations.

III. Exemplary Transaction Database Embodiments

Figure 4:
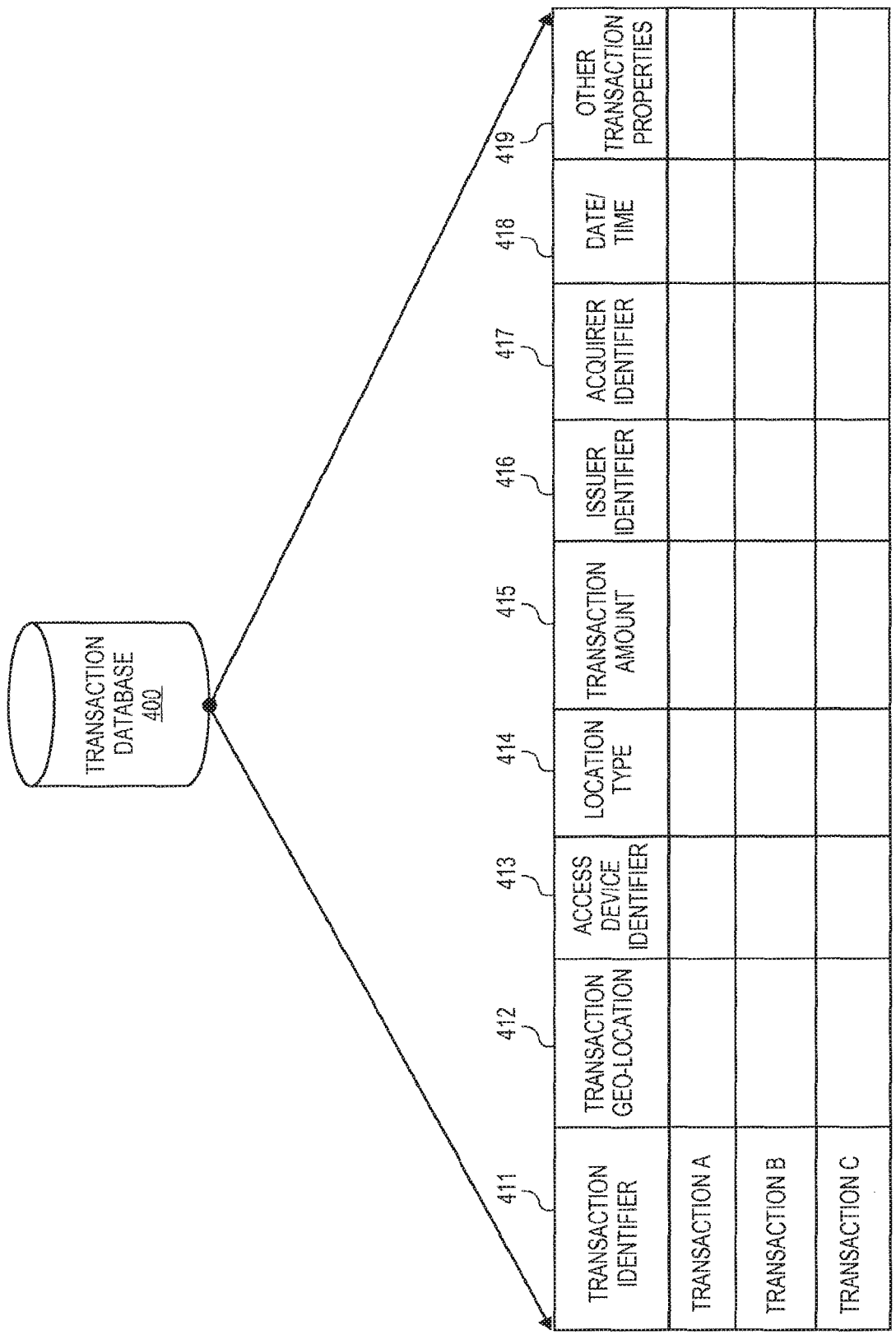
FIG. 4 shows a diagram of an exemplary transaction database in one embodiment of the invention.

With reference to FIG. 4, a more detailed illustration of an exemplary embodiment of a transaction database 400 is shown. The transaction database 400 may be configured to comprise some or all transaction data received by a payment processing network 200. Transaction data may be electronically retrieved from authorization request messages, authorization response messages, clearing and settlement messages, or any other suitable sources. Transaction data stored in the transaction database 400 may include a transaction identifier 411, transaction geo-location 412, access device identifier 413, location type 414, transaction amount 415, issuer 416, acquirer 417, date/time 418, or other transaction properties 419. In some embodiments of the invention, transaction database 400 may be anonymized, so that no sensitive data is stored.

Transaction identifier 411 may be any suitable identifier for a transaction. In some embodiments, transaction identifier 411 may be unique in the transaction database 400. In some embodiments, transaction identifier 411 may be operative to retrieve the transaction from another, non-anonymized transaction database (not shown).

Transaction geo-location 412 may be any information associated with the geo-location of a transaction. Transaction geo-location 412 may, for some transactions, be sufficient to identify a physical location where the transaction occurred. In these cases, transaction geo-location 412 may store the corresponding geo-location. Alternately, in some embodiments of the invention, transaction geo-location 412 may not specify an exact physical location, but rather an area. For example, the transaction geo-location may comprise a postal code (e.g., ZIP code), center geo-location and radius, or list of possible geo-locations.

The access device identifier 413 may be a unique identifier that may be used to identify an access device used to conduct the transaction. In some embodiments of the invention, a contactless access device associated with an access device identifier 413 may also have a corresponding contactless device identifier 311 in location database 300. In such embodiments, the access device identifier 413 may be used to retrieve location data corresponding to the access device. Alternately, the contactless device identifier 311 may be used to retrieve transaction data for one or more transactions conducted using the access device.

Location type 414 may indicate a category or other classifier for a type of location associated with the contactless access device. For example, in some embodiments, the merchant type may Merchant Category Code (MCC) for a merchant associated with the contactless access device. In some embodiments, Location type 414 may also be used to identify whether the location corresponds to a bank branch, ATM, or merchant.

Transaction amount 415 may indicate an amount paid for the transaction. For example, the transaction amount 415 may indicate a currency and a value in the currency paid.

Issuer identifier 416 may be a unique identifier to an issuer associated with an account associated with the contactless consumer device which was used to conduct the transaction. In some embodiments, the issuer identifier may be a name of an issuer or an identification number such as a BIN (bank identification number). In some embodiments of the invention, an issuer associated with an issuer identifier 416 may have a corresponding entry in mapping database 500 comprising one or more mapping parameters. In such embodiments, issuer identifier 416 may be used to retrieve mapping parameters corresponding to the issuer. Alternately, the issuer identifier 416 may be used to retrieve transaction data for one or more transactions associated with the issuer.

The acquirer identifier 417 may be a unique identifier associated with an acquirer associated with the merchant that operates the access device for a transaction. In some embodiments, the issuer identifier may be a name of an acquirer or an identification number such as a BIN (bank identification number). In some embodiments, if an acquirer and an issuer are the same financial institution, the acquirer identifier 417 and the issuer identifier 416 may be the same.

Date/Time 418 may comprise a timestamp or other indication of the date and time a transaction was conducted.

Other transaction properties 419 may include any other properties associated with the transaction. For example, in some embodiments, other transaction properties may include a merchant identifier such as the merchant's name, a consumer identifier such as the consumer's name, payment information used to conduct the transaction, or any other information associated with the transaction.

IV. Exemplary Mapping Database Embodiments

Figure 5:
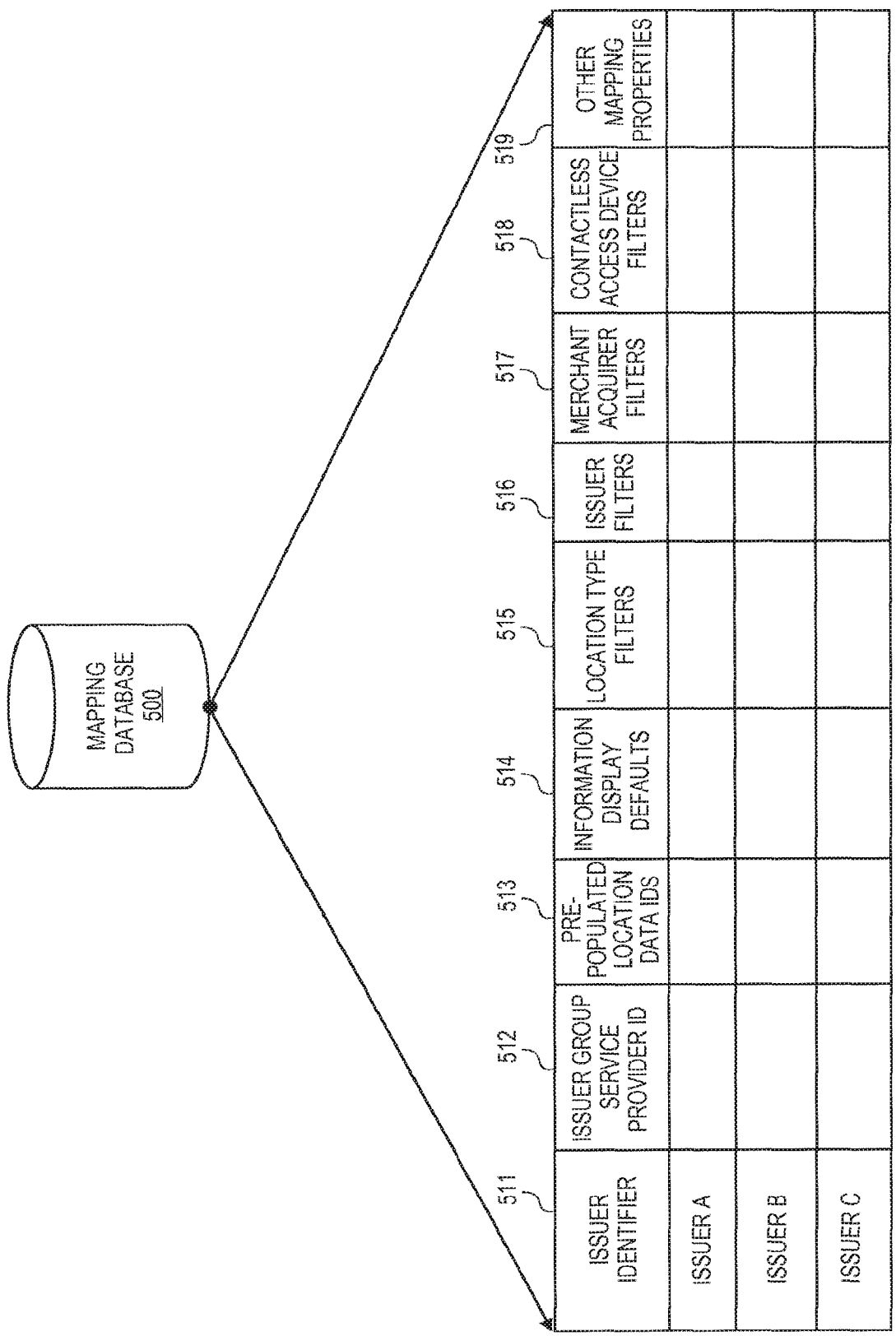
FIG. 5 shows a diagram of an exemplary mapping database in one embodiment of the invention.

With reference to FIG. 5, a more detailed illustration of an exemplary embodiment of a mapping database 500 is shown. The mapping database 500 may be configured to comprise some or all mapping parameters electronically received by payment processing network 200 and associated with an issuer or other entity. In general, mapping parameters may be used when generating map data. Typically, mapping parameters may be retrieved from an issuer, but may also be electronically received from any other suitable source. Mapping parameters stored in the mapping database 500 may include an issuer identifier 511, an issuer group service provider identifier 512, one or more pre-populated location data identifiers 513, one or more information display defaults 514, location type filters 515, issuer filters 516, merchant acquirer filters 517, contactless access device filters 518, or other mapping parameters 519.

Issuer identifier 511 may be unique identifier assigned to each issuer. In some embodiments of the invention, an issuer identifier 511 may be assigned by the payment processing network when mapping parameters for an issuer are added to the database. Alternately, in other embodiments, issuer identifier 511 may be assigned by a third party, and be used for other purposes. For example, in various embodiments, the issuer identifier may be a bank identification number (BIN) or automated clearinghouse (ACH) routing number.

Issuer group service provider identifier 512 may be an identifier that is unique to each issuer group service provider. An issuer group service provider may be an organization which manages location services for two or more issuers.

Pre-populated location data identifiers 513 may include one or more identifiers for pre-populated location data. Pre-populated location data may be any location data not provided by the issuer but by the payment processing network or third party. For example, in some embodiments of the invention, the payment processing network will gather and maintain contactless access device location data independently of any data electronically received from issuers. Such location data may be offered to issuers, so that if an issuer wants to include the location data in maps generated for the consumers associated with the issuer, the issuer may specify a parameter noting the identifier of the pre-populated location data. For all identifiers selected by the issuer, contactless access devices contained in the corresponding location data may be displayed to the user. For example, the payment processing network may maintain location data corresponding to locations where payment cards associated with the payment processing network can be purchased or reloaded.

Information display defaults 514 may include one or more default values to indicate information that can be displayed by default to consumers associated with the issuer. For example, in some embodiments, the issuer may define information display defaults to indicate whether a long form or short form description should be shown on a generated map, whether a phone number should be displayed, or any other parameter relating to the presentation of information contained in map data generated for the consumer.

Location type filters 515 may include filters based on the location type of the location where the contactless access device is located. For example, in one embodiment, the issuer may specify that merchants with a given Merchant Category Code (MCC) should not be included in map data generated for consumers associated with the issuer. Issuer filters 516 may include filters based on an issuer identifier associated with the contactless access device. Similarly, merchant acquirer filters 517 may include filters based on the acquirer identifier of a merchant associated with a contactless access device. Contactless access device filters 518 may include filters on the make, model, or technology used by contactless access devices.

Other mapping parameters 519 may include any other type of mapping parameter that may be used to modify map data generated for consumers associated with the issuer. For example, in some embodiments, other mapping parameters may include filters on multiple location data attributes, or filters that may be composed using Boolean logic.

In some embodiments, other mapping parameters 519 may also include properties of an application or web site provided to consumers associated with the issuer. For example, the name of the application or title of the website may be configurable. In addition, other mapping parameters 519 may also include branding associated with the issuer for use with the application or web site.

V. Exemplary Methods

Figure 6:
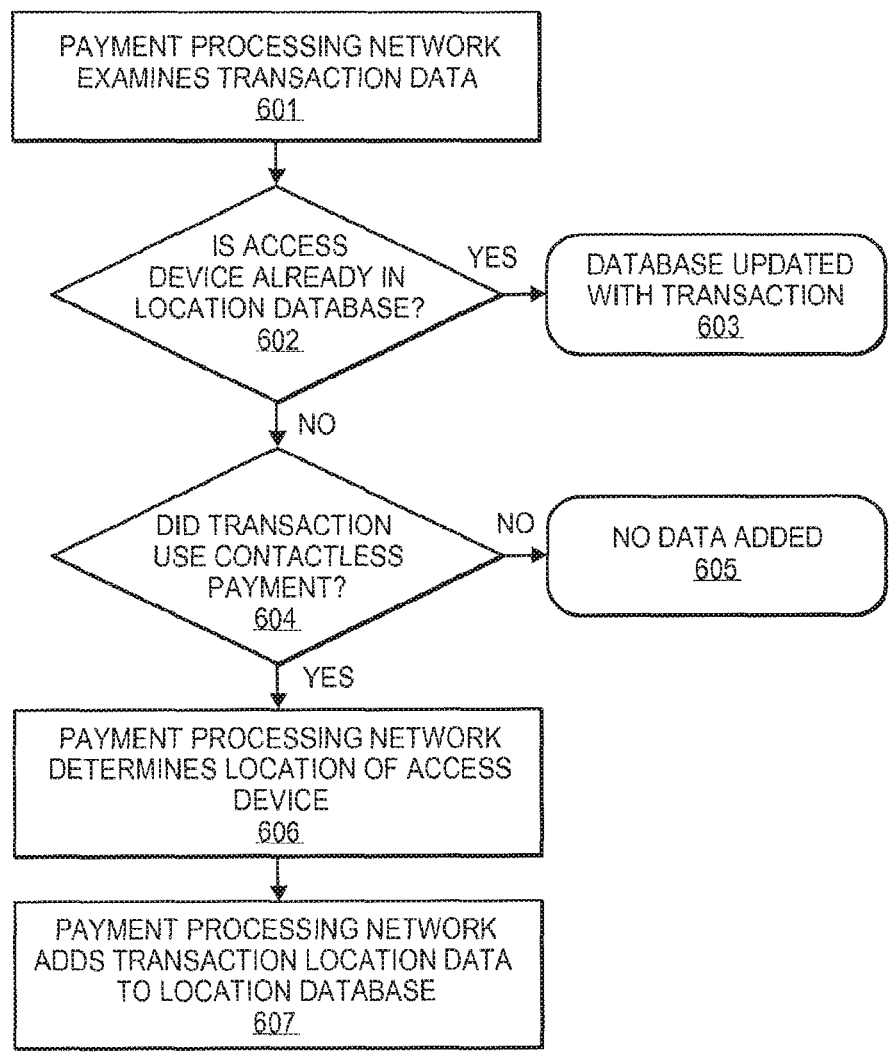
FIG. 6 illustrates a method for adding a transaction to the location database.

FIG. 6 illustrates an exemplary use case flow for adding a transaction to the location database. Reference is also made to the elements in FIGS. 1-4. In various embodiments of the invention, the flow in FIG. 6 may be performed by the location server computer, or other suitable computer. Typically, the flow is performed periodically to update and/or add information regarding contactless access devices to a location database. Alternately, in other embodiments, the flow in FIG. 6 may be performed when the payment processing network receives data relating to a transaction.

At step 601, the location server computer 201 electronically receives and examines transaction data. In some embodiments, the transaction data may be stored in the transaction database 400. Alternately, the transaction data may be electronically received from another source, such as from an access device and/or via a communications network 103. The transaction data may contain information regarding a transaction, including, but not limited to, a consumer, a merchant identifier, an amount of the transaction, a geo-location where the transaction was conducted, or any transaction data (e.g., data that is described with respect to the data fields described in FIG. 4).

In some embodiments, the transaction data may be electronically received by the server computer in the payment processing network 200 in an authorization request message. The authorization request message may have been generated by an access device 112 located at the merchant 110, and may have been routed through an acquirer computer 108. The authorization request message may comprise a transaction amount, an access device identifier, a merchant category code, a service code, an expiration date, geolocation data, and other information. In such embodiments, the transaction data may be electronically received in real time by the server computer during the transaction. In other embodiments, the transaction data can be received after a transaction has taken place.

At decision step 602, the location server computer 201 determines if the access device 112 is already in the location database 300. In some embodiments, the location server computer 201 may check if location data exists corresponding to an access device identifier associated with the transaction.

If so, at step 603 the location information in the location database 300 may be updated with information in the transaction data. For example, if the transaction data indicates that the location of the contactless access device has moved, the location server computer 201 may update the corresponding geodata in the location data in the location database 300 accordingly. In other cases where the location data and transaction data differ, the location data may be immediately updated or updated after a threshold of time. For example, the information may be updated after 3 months of seeing a disparity between the location data in the location database 300 and the transaction data that is continuously received from that access device 112 during that period of time. Otherwise, if the access device 112 is not already in the location database 300, the method proceeds to decision step 604.

At decision step 604, the location server computer determines if the transaction was conducted using a contactless payment mechanism. In some embodiments of the invention, this may be determined by a contactless indicator flag that is present in the transaction data. In other embodiments, the process of determining if the transaction was conducted with a contactless payment device 32 may be determined by another property of the transaction, such as the make and/or model of access device used to conduct the transaction.

At step 605, if the transaction was not performed using a contactless access device, the process terminates with no data added or updated in the location database. If the transaction used contactless payment or was performed using a contactless access device, the method proceeds to step 606.

At step 606, the payment processing network 200 determines the location of the access device 112. In some embodiments, and for some transaction data, the geo-location of the transaction may be included in the transaction data. For example, a latitude-longitude pair may be included in the transaction data, which may be present in an authorization request message. Alternately, an address for the access device 112 may be included in the transaction data. In other embodiments, the location of the transaction may be derived from other data present in the transaction data, such as an IP address used by the contactless access device 112. In yet other embodiments, the location may be triangulated based on the strength of cell phone reception from cell towers.

At step 607, the location server computer 201 in the payment processing network 200 adds the transaction location data to the transaction database 400. The location data may comprise any suitable data from the transaction data. For example, if the transaction data is derived from the transaction database illustrated in FIG. 4 and added to the location database 300 illustrated in FIG. 3, at least the access device identifier, transaction geo-location, location type, and issuer identifier, and acquirer identifier fields of the transaction data may be added to the data for a particular access device in the location database 300.

Figure 7:
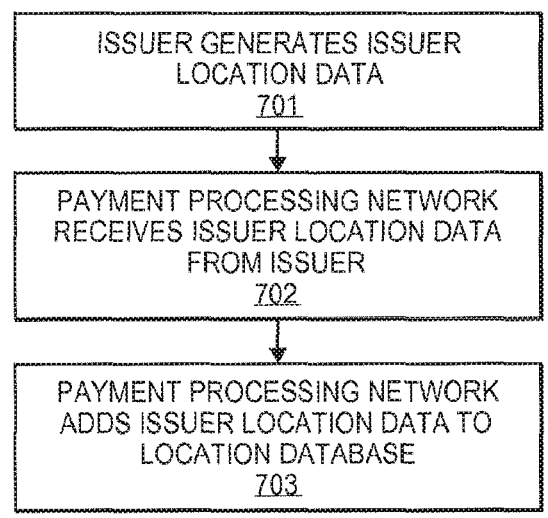
FIG. 7 illustrates a method for adding location data to a location database.

FIG. 7 illustrates an exemplary use case flow for adding location data to a location database. In the embodiment illustrated in FIG. 7, the issuer generates data including location data and electronically transmits it to the payment processing network 200. In various other embodiments of the invention, the flow in FIG. 7 may be performed for one or more issuers, acquirers, merchants, or other parties in order to provide location data associated with the one or more issuers, acquirers, merchants, or other parties to the location database.

At step 701, an issuer 106 generates issuer location data associated with the issuer. The issuer location data may correspond to the locations of access devices that are associated with the issuer 106. The location data may be generated from any suitable source at the issuer. In some embodiments, some issuers may maintain a database of contactless access devices associated with the issuer. For example, issuers that offer contactless ATM withdrawal or deposit services may maintain a database of contactless ATMs. Location data corresponding to the contactless ATMs may be included in the issuer location data. In some embodiments, the issuer may also maintain a database of merchants associated with the issuer. For example, in the case of an issuer-acquirer, the database of merchants may contain merchants for which the issuer-acquirer provides acquirer services. Location data corresponding to the database of merchants may also be included in the issuer location data.

In some embodiments of the invention, the issuer location data may be included in a location data file. The location data file may be a file in tabular or any other suitable format for holding location data for one or more contactless access devices. In some embodiments, the format of the location data file may be defined by the payment processing network, so that multiple issuers may use the same location data file format to transmit location data to the payment processing network.

After generating the issuer location data, the issuer 106 transmits the issuer location data, along with any contactless access device information (e.g., a contactless access device ID) to the payment processing network 200.

At step 702, the payment processing network 200 electronically receives the issuer location data. In some embodiments of the invention, the issuer 106 may electronically transmit the issuer location data and access device data directly to the location server computer 201.

At step 703, the location server computer 201 in the payment processing network 200 adds the issuer location data to the location database 300. Typically, the issuer location data may have one or more fields in common with the location data fields stored in the location database, such as the location name, location geodata, and location type. The issuer location data may also have one or more fields not explicitly present in the location database. Such fields may be added to the "Other Location Properties" field of the location data. In some embodiments of the invention, the contactless access device identifier may be provided in the issuer location database. In this case, the same contactless access device identifier may be used in the location database. Alternately, the location server computer may generate a unique contactless access device identifier for one or more access devices in the issuer location data.

In some embodiments of the invention, the flow described in FIG. 7 may be performed multiple times by an issuer, acquirer, or other party. For example, an issuer may periodically add contactless access devices to the location database when new ATMs or bank branches are opened. In some embodiments, issuers may also be able to submit updated issuer location data to update location data stored in the location database. The location server computer may accordingly update existing data in the location database rather than creating new location data.

Figure 8:
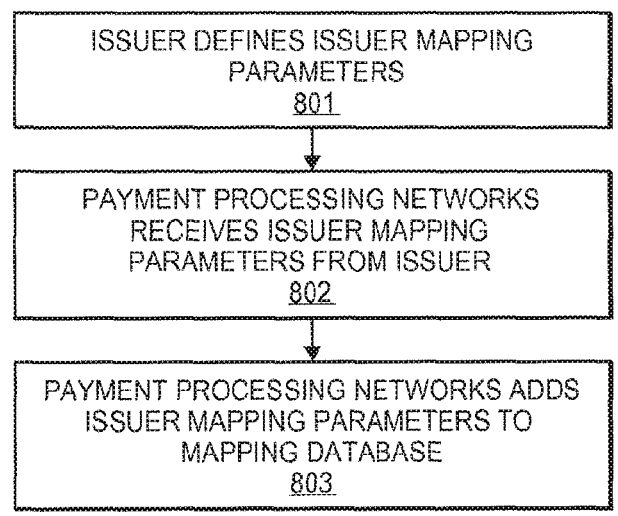
FIG. 8 illustrates a method for adding issuer mapping parameters associated with an issuer to a mapping database.

FIG. 8 illustrates an exemplary use case flow for adding issuer mapping parameters associated with an issuer 106 to a mapping database 500. In the embodiment illustrated in FIG. 8, the issuer defines mapping parameters for consumers associated with the issuer. However, in other embodiments, the method described in FIG. 8 may be performed by an issuer group service provider (issuer GSP) for consumers associated with any issuer in the GSP, or may be performed by an individual consumer to define custom mapping parameters for the consumer.

At step 801, the issuer 106 defines issuer mapping parameters. The issuer mapping parameters may define parameters affecting map data in the generation of maps on a communications device 102 for a consumer 101. Issuer mapping parameters may include, for example, pre-populated location data identifiers, information display flags, and filters. The issuer 106 may define mapping parameters based on perceived interests and/or needs associated with consumers. For example, an issuer 106 may filter contactless access devices based on the contactless technology used by the issuer. Contactless access devices not using a compatible technology to the issuers may be removed or hidden from the map data. Alternately, an issuer associated with a particular geographical area may filter contactless access devices outside of that area. The issuer may electronically transmit the mapping parameters to the payment processing network 200, to the location server computer 201, or directly add the mapping parameters to the mapping database 500.

At step 802, the payment processing network 200 electronically receives issuer mapping parameters from the issuer 106. Such parameters may be electronically transmitted from the issuer 106 to the payment processing network 200.

At step 803, the payment processing network 200 adds issuer mapping parameters to the mapping database 500. Typically, the issuer mapping parameters may have one or more parameter in common with the mapping parameters stored in the location database 300, such as the pre-populated location data identifiers, filters, or display flags. The issuer mapping parameters may also have one or more parameters not explicitly present in the mapping database. Such fields may be added to the "Other Mapping Properties" field of the mapping database. In some embodiments of the invention, the issuer identifier may be provided in the issuer mapping parameters in order to uniquely identify the issuer. In this case, the same issuer identifier may be used in the mapping database 500. Alternately, the location server computer 300 may generate a unique issuer identifier for one or more issuers in the mapping database 500.

The method described for FIG. 8 may be performed additional times for each issuer to update the mapping database. For example, when an issuer adds support for a new technology to contactless consumer devices, the issuer may update the mapping parameters to include contactless access devices supporting the technology in generated map data.

Figure 9:
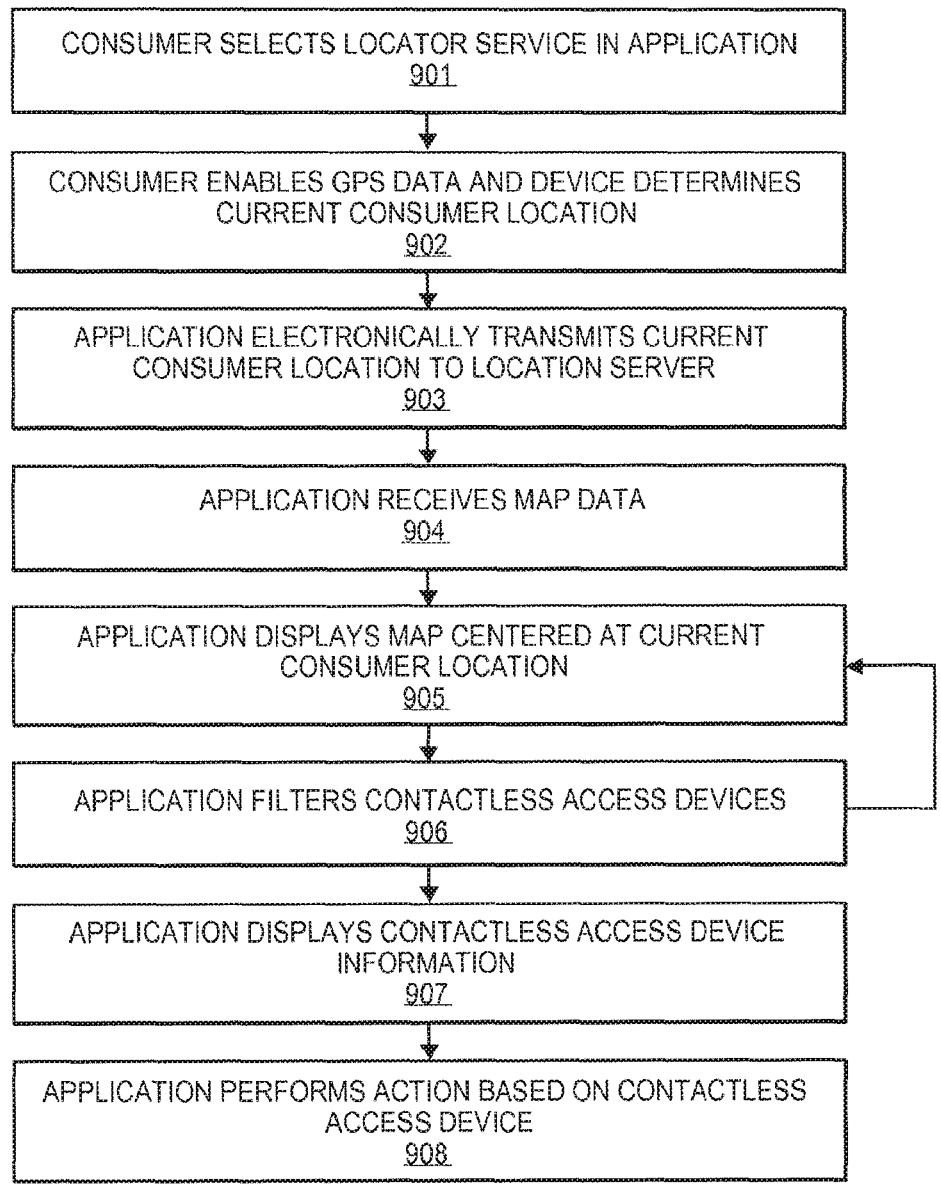
FIG. 9 illustrates a method for providing location services to consumers associated with an issuer.

FIG. 9 illustrates an exemplary method for providing location services to consumers associated with an issuer. In some embodiments, the consumer may connect to the payment processing network 200 or location server computer 201 using an application or web browser running on a communications device 102. In the embodiment illustrated in FIG. 9 and described below, the application may be a mobile application and the communications device may be a mobile phone. However, other embodiments of the invention may use any application or web browser, and communications device.

In some embodiments of the invention, the application used by the consumer 101 may be branded by the issuer 106. For example, in some embodiments, a payment processing network 200 or third party may implement an application for connecting to the location server computer 201 and providing location services. The payment processing network 200 or third party may make the application available to issuers, so that each issuer may brand the application with its logo, color scheme, etc. Alternately, in other embodiments, the issuer may use a custom application. In some embodiments, the issuer may tag the application with an issuer identifier or other information, so that a payment processing network 200 or location server computer 201 may identify that the application is associated with an issuer 106. In other embodiments, the consumer 101 using the application may indicate an issuer 106.

Figure 10:
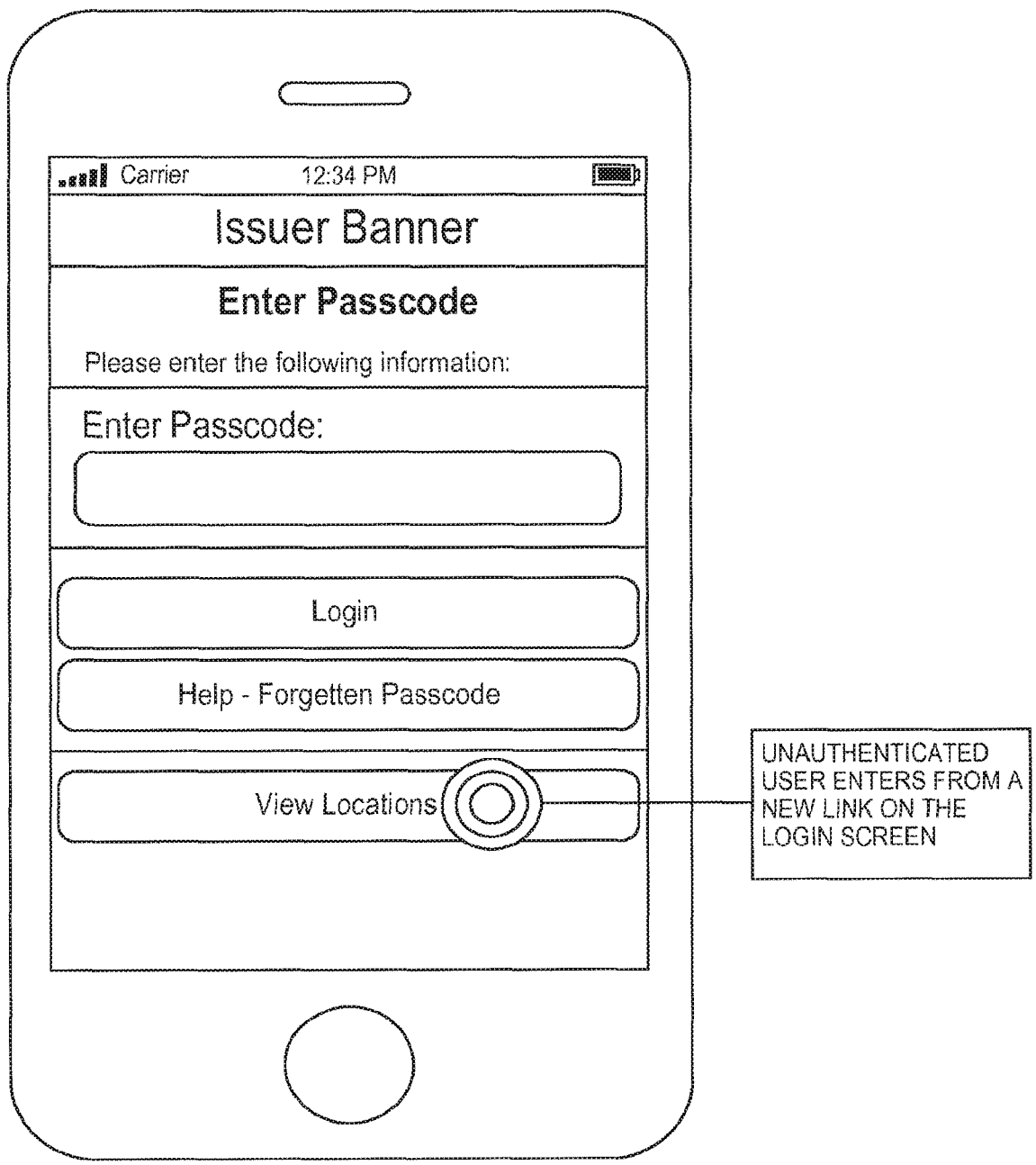
FIGS. 10-23 illustrate user interface screenshots according to embodiments of the invention.
Figure 11:
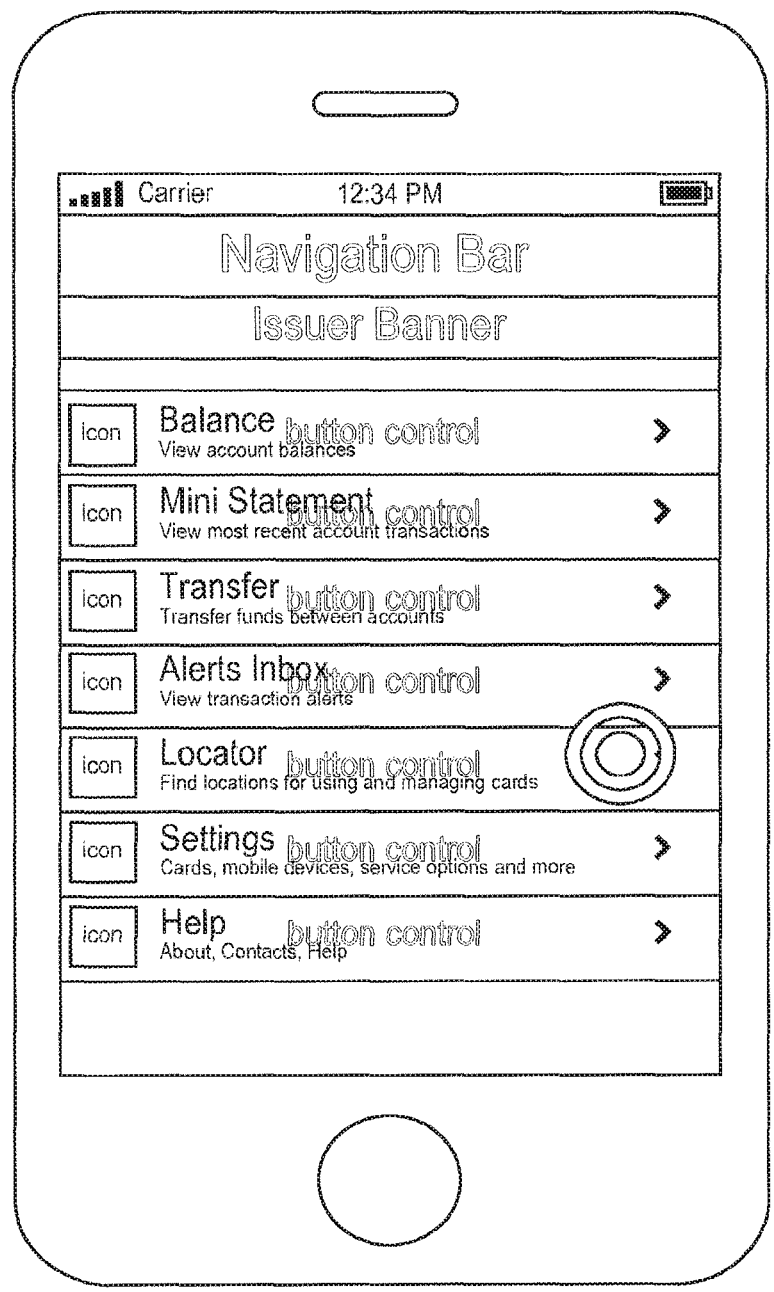
Figure 12:
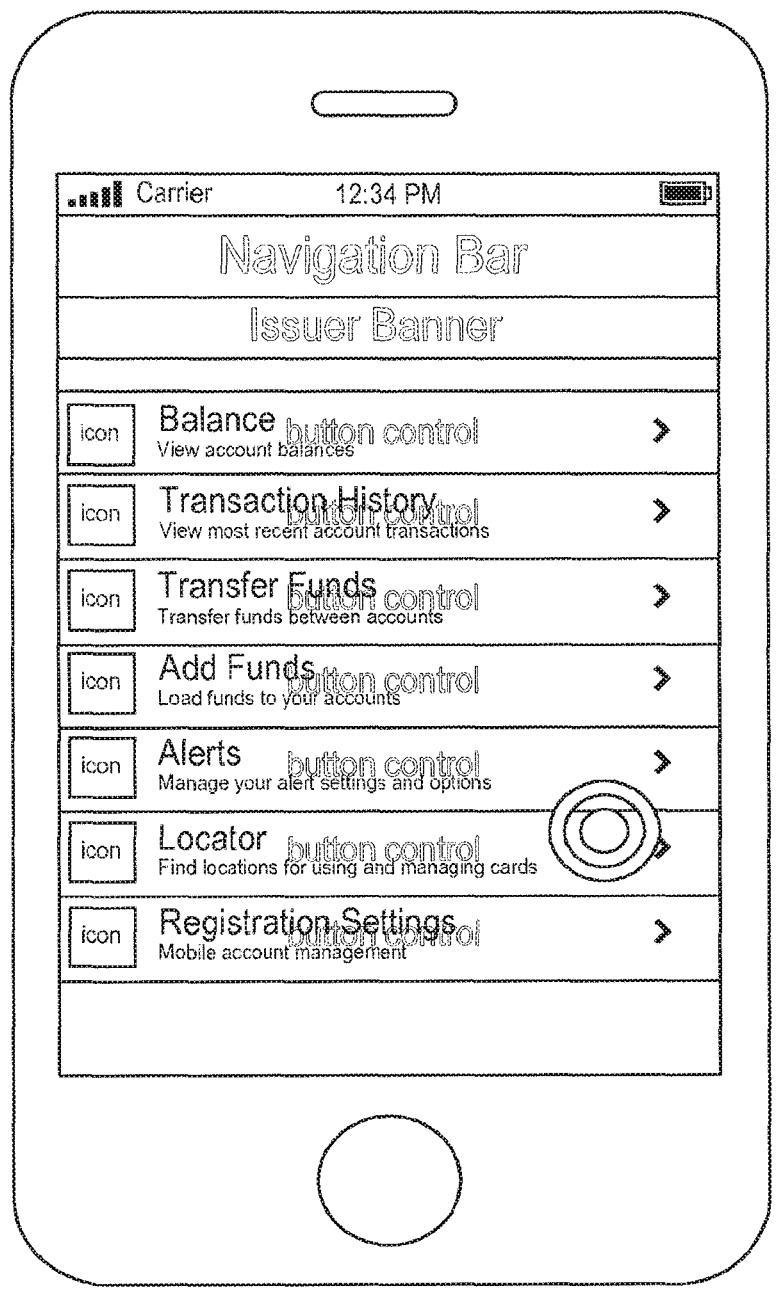

At step 901 of the method, the consumer 101 selects a locator service in an application running on a communications device 102. One exemplary diagram of step 901 is illustrated in FIG. 10, wherein an unauthenticated user selects a "View Locations" button on a login screen. Alternate embodiments are shown in FIG. 11 and FIG. 12, wherein a locator menu item may be selected after logging in to the mobile application.

Figure 13:
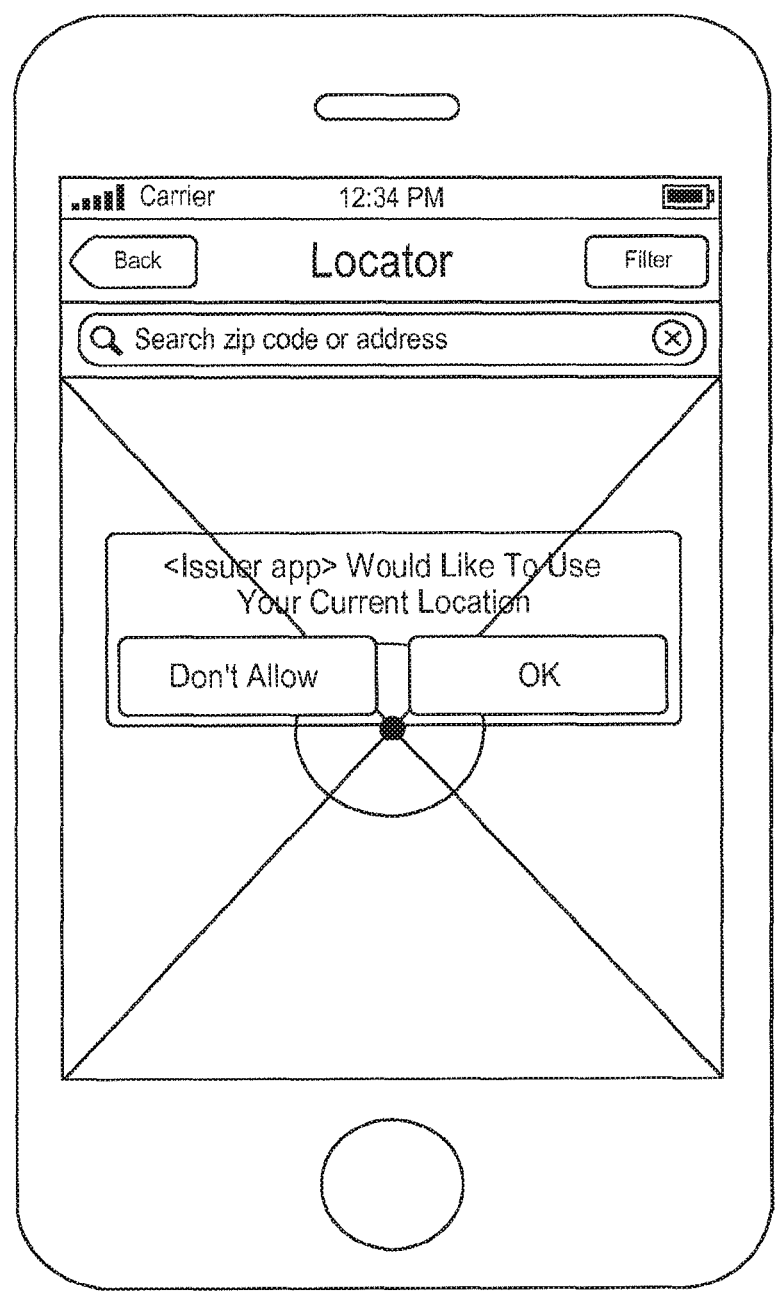
Figure 14:
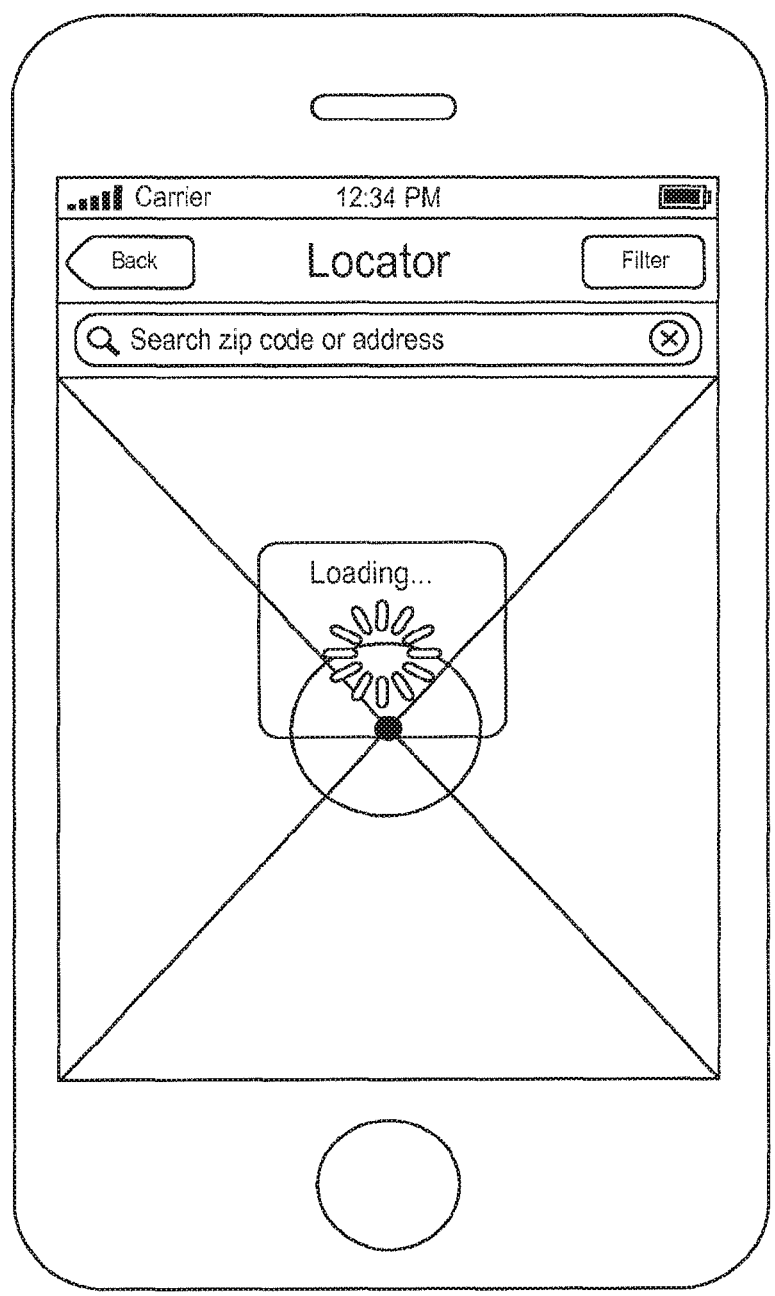

At step 902 of the method, the consumer 101 enables GPS data from a GPS receiver associated with the communications device 102 and determines a current consumer location. In some embodiments of the invention, the application may determine if the GPS receiver is disabled, and if so prompt the consumer to enable the GPS receiver. FIG. 13 shows an exemplary screen that may be shown to prompt the consumer. The device then determines the current consumer location. A loading screen, such as is shown in FIG. 14, may be displayed until a current location is determined by the GPS receiver. Alternately, in some embodiments, a current location may be determined using other methods, such as cellular tower triangulation, proximity of wireless networks, or other satellite navigation methodologies.

Figure 17:
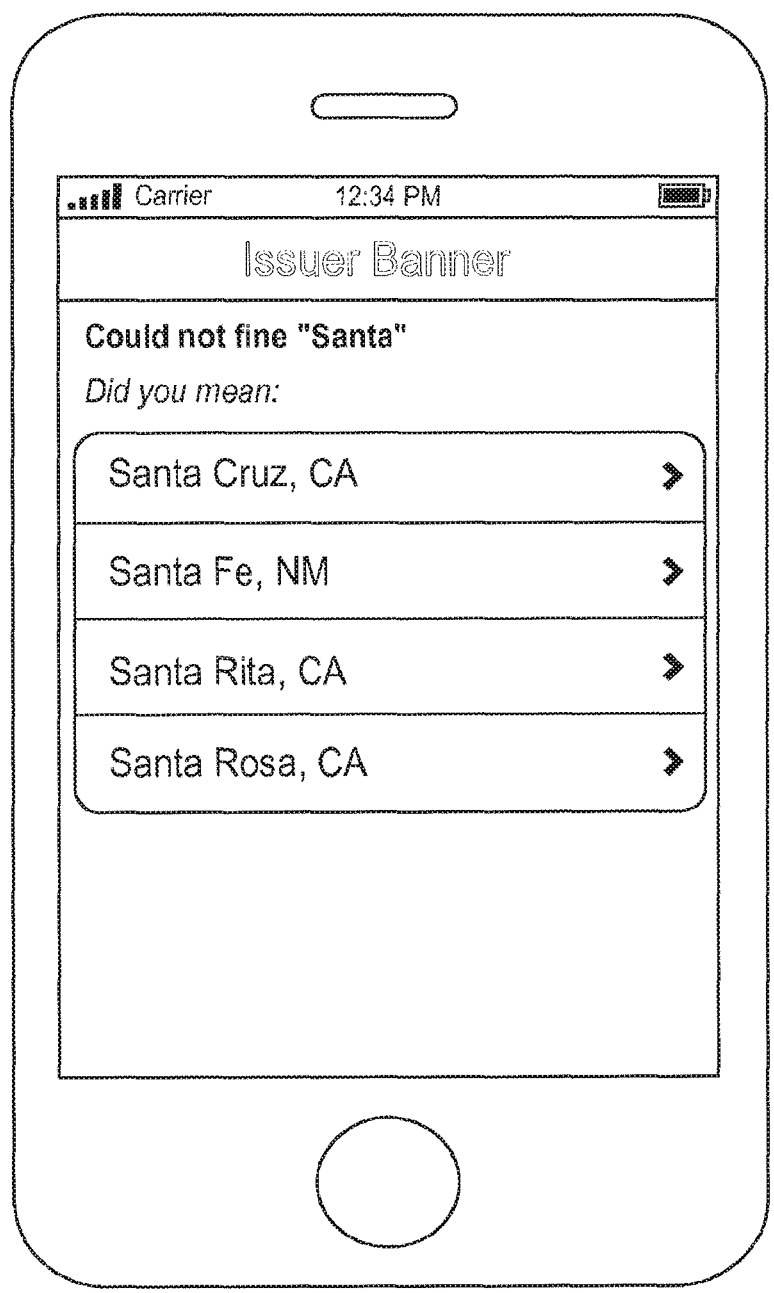

In some embodiments of the invention, the consumer 101 may manually enter the current consumer location. The location entered may be of any suitable form, such as a latitude-longitude pair, an address, a postal code, or a city. If the specified location could not be found, or if multiple results were found for the specified location, the application may prompt the consumer with a list of similar matches. FIG. 17 shows an exemplary screen that may be shown to consumers in one embodiment of the invention.

At step 903, the communications device 102 electronically transmits the current consumer location to the location server computer 201. In some embodiments of the invention, the current consumer location may be included in the JSON location data request message format described earlier. In some embodiments of the invention, the location server computer 201 may have a uniform resource locator (URL), IP address, or other network address programmed into the application. The application may transmit the current consumer location using any suitable protocol, such as the TCP/IP protocol, UDP protocol, or other protocol known in the art, over a wireless or wired connection medium. In some embodiments, the application may include an indication of an issuer identifier or issuer group service provider identifier with the location data. This identifier may be determined by the branding of the application. Alternately, the application may include information associated with the consumer, such as a consumer identifier, with the current consumer location.

At step 904, the application on the communications device 102 electronically receives the map data from the location server computer 201. One embodiment of map data included in a JSON location data response message is described earlier. In other embodiments of the invention, map data may comprise any data operable by the application to display a map of locations of contactless access devices nearby to the current consumer location. Map data may also include information regarding the nearby contactless access devices. In some embodiments, map data may include any number of fields in the location database associated with a contactless access device. Further data included in the map data may include an address, phone number, or customer ratings of a merchant or bank associated with the contactless access device. This data may be used to display information on the device. Map data may also include data usable to filter contactless access devices, so that one or more of the nearby contactless access devices may be hidden from the map based on a filter.

Figure 15:
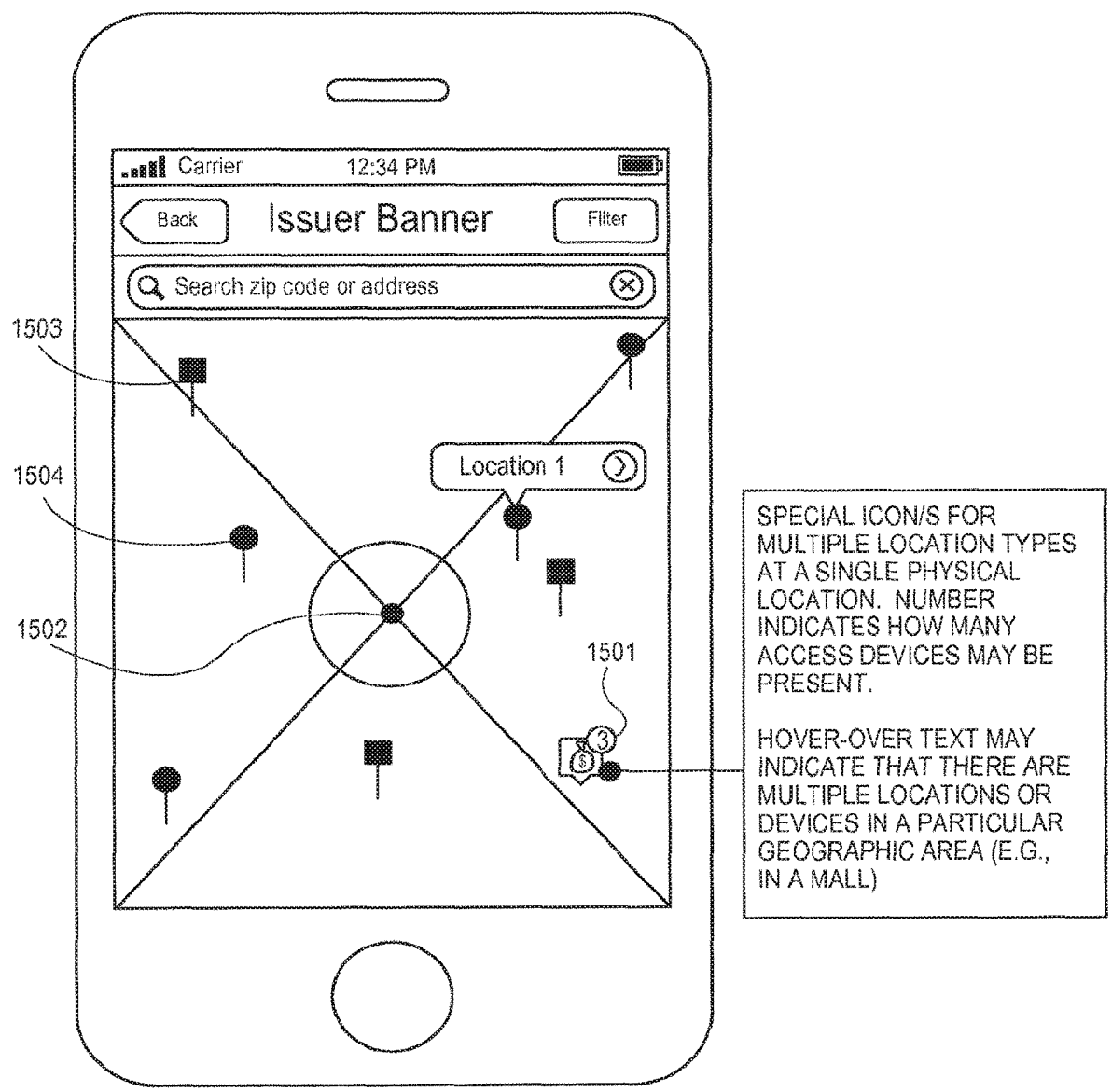

At step 905, the application on the communications device 102 displays a map centered at the current consumer location. FIG. 15 illustrates an exemplary map that may be displayed. The map may comprise a marker 1502 illustrating the current consumer location, and multiple markers 1503 and 1504 illustrating the locations of contactless access devices In some embodiments of the invention, merchants, banks, ATMs, or other institutions with multiple contactless access devices may be represented by a single marker. In some embodiments of the invention, as illustrated in icon 1501, special icons may be used to depict multiple location types at a single physical location. In some embodiments, hover-over text may indicate that multiple contactless access devices are present at the shown location.

Figure 16:
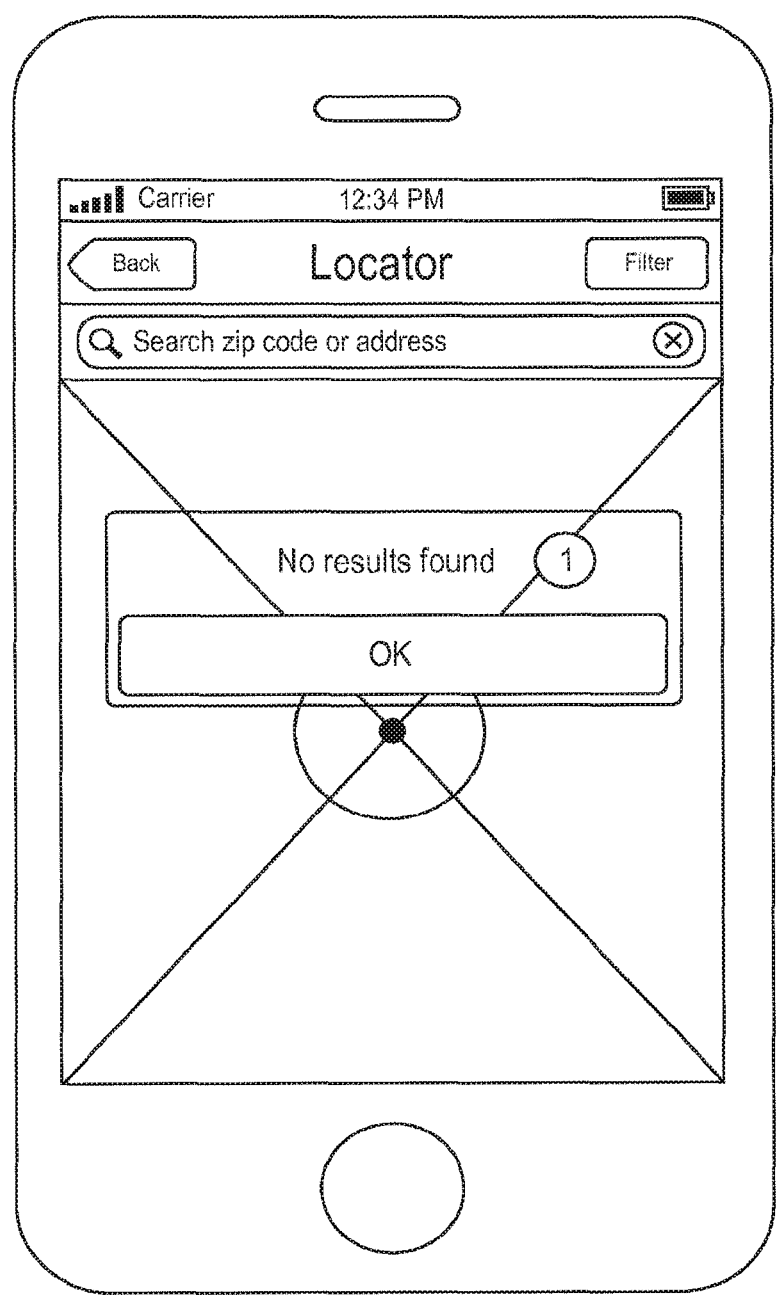

In some embodiments, and under some conditions, an error may be indicated. FIG. 16 shows one possible error screen in embodiments of the invention. Error conditions may include: no contactless access devices found, no wireless signal, current location cannot be determined, map data unavailable, access device information unavailable, and location server unavailable. In some embodiments, the user may be prompted to accept the error or restart the application.

Figure 18:
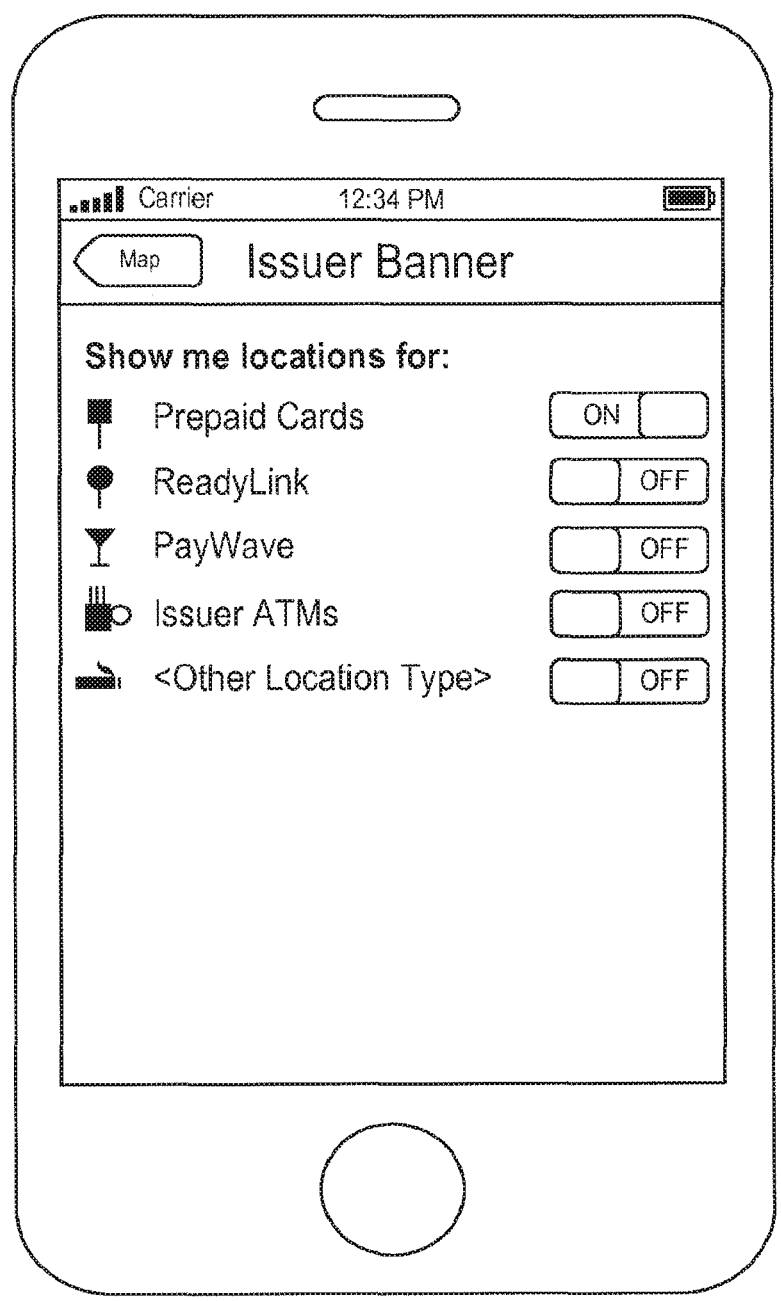
Figure 19:
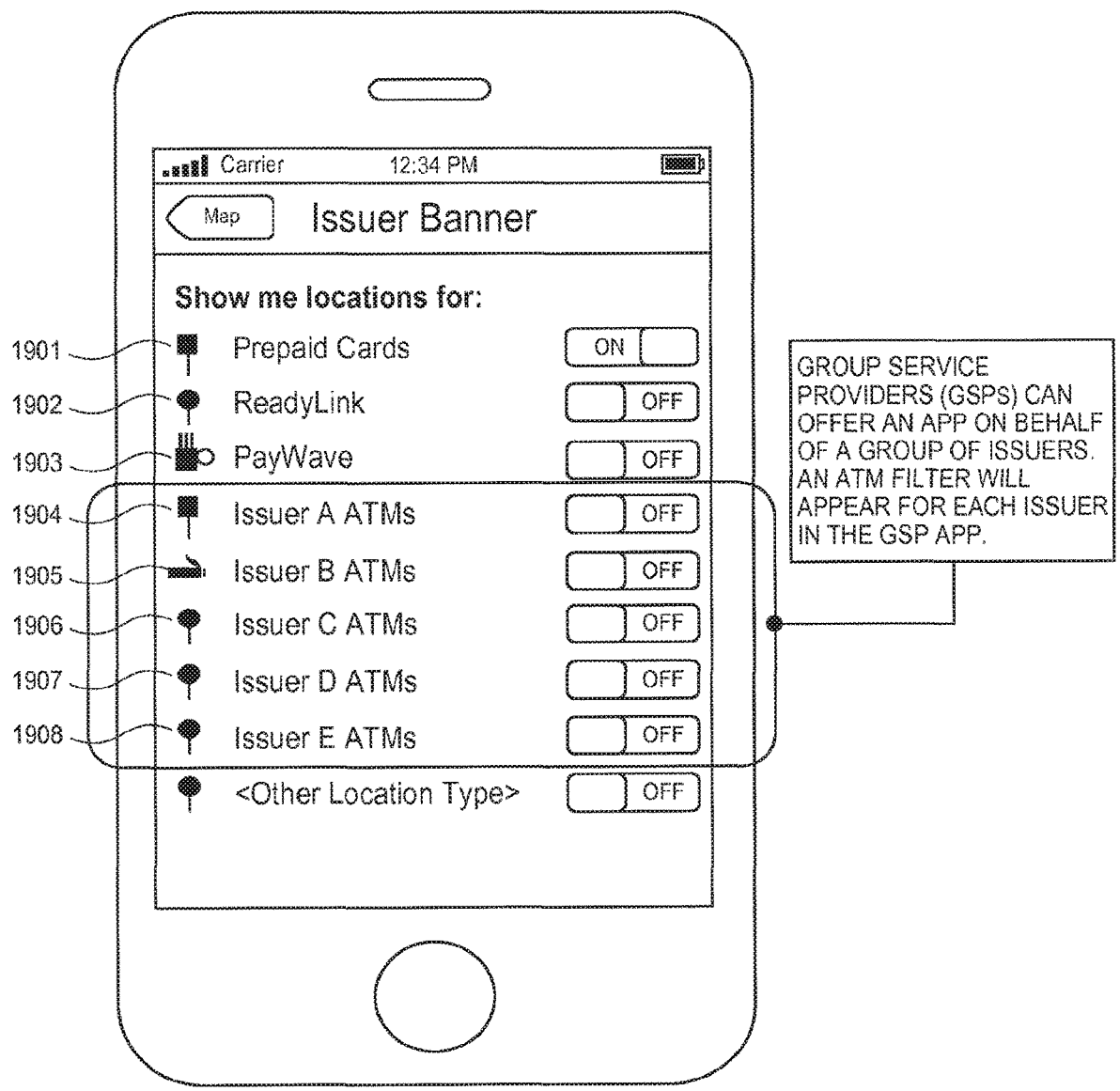

At step 906, the consumer 101 may define filters on the contactless access devices present in the map data. Filters may include those shown in FIG. 18, such as locations associated with access devices which accept prepaid devices 1901, loadable prepaid devices 1902, contactless devices 1903, and debit devices for ATMs and the like. In some embodiments, when the issuer is part of an issuer group service provider (GSP), filters may also include ATMs, bank branches, or other categories associated with the GSP. In an exemplary embodiment shown in FIG. 19, filters may include issuer ATMs corresponding to various issuers A-E 1904-1908. When filters are defined, the map displayed on the communications device 102 in step 905 may be updated to hide markers not meeting the criteria discussed.

Figure 20:
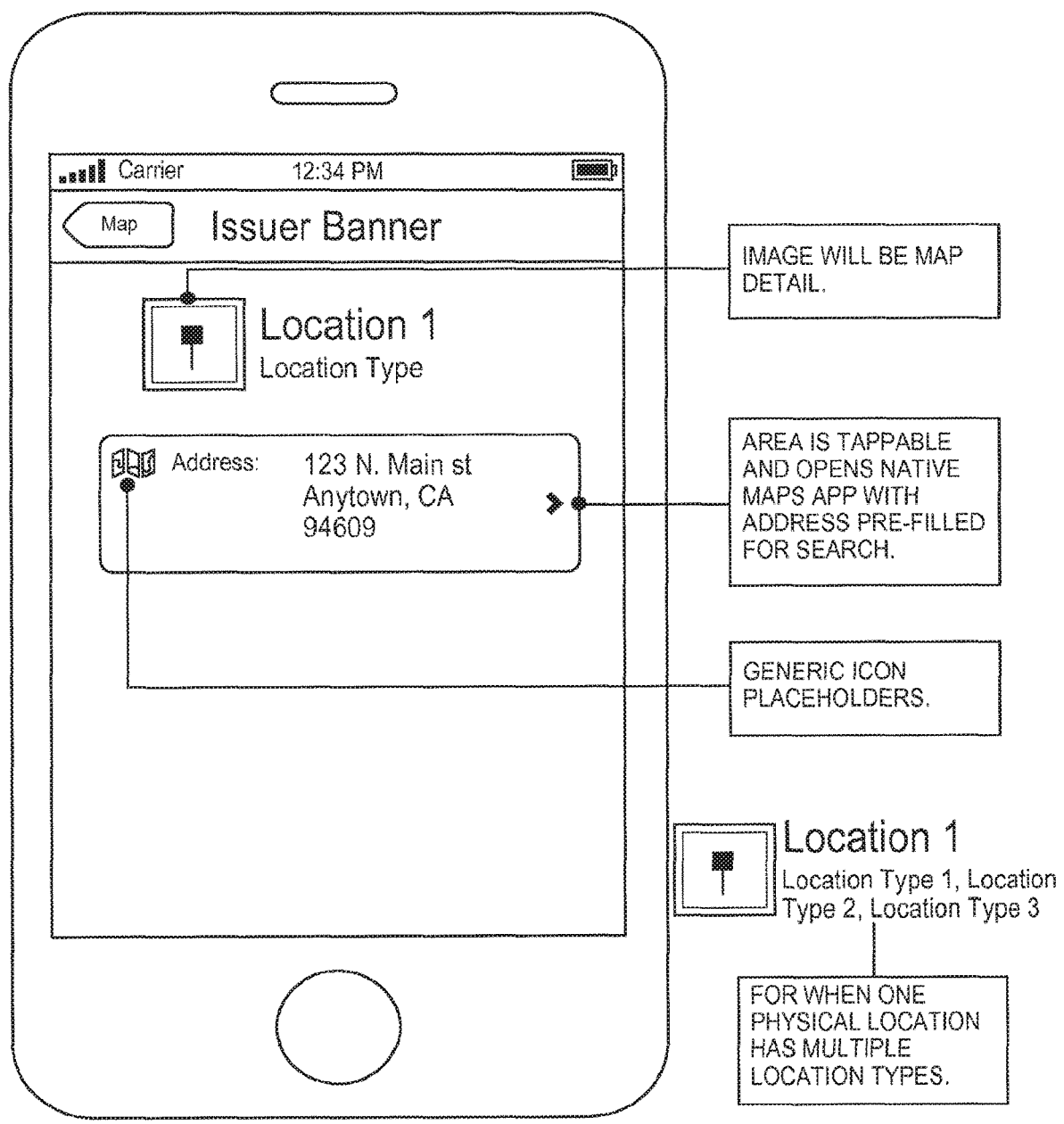

At step 907, the application on the communications device 102 displays additional information regarding a marker selected by the consumer 201. If the marker corresponds to a single contactless access device operated by a merchant, the merchant information that may be displayed may include the merchant's location on a small map, the merchant address, phone number, merchant ratings, hours, or other information. In some embodiments, the area used to display the address or other information may be tapped by the consumer to open another application. FIG. 20 is an exemplary embodiment illustrating the display of merchant information. Similar information may be displayed if the contactless access device is operated by a bank, ATM, or other institution.

Figure 21:
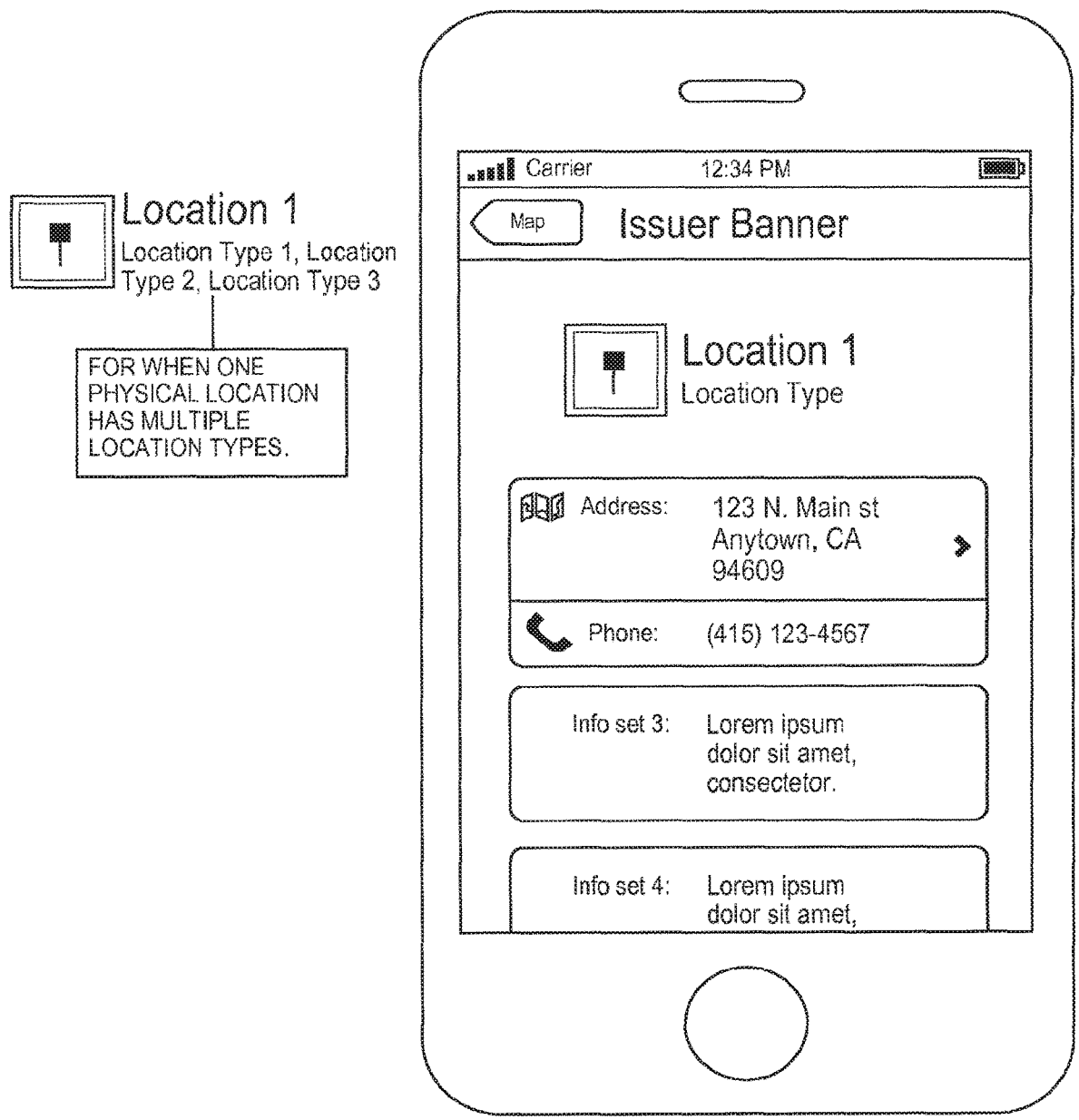

In some cases, multiple contactless access devices corresponding to different merchants may share the same geolocation. In some embodiments of the invention, information relating to all merchants may be displayed on a single page. For example, the addresses and phone numbers of all merchants may be displayed. An exemplary embodiment showing a display of multiple pieces of information for multiple merchants may be found in FIG. 21.

Figure 22:
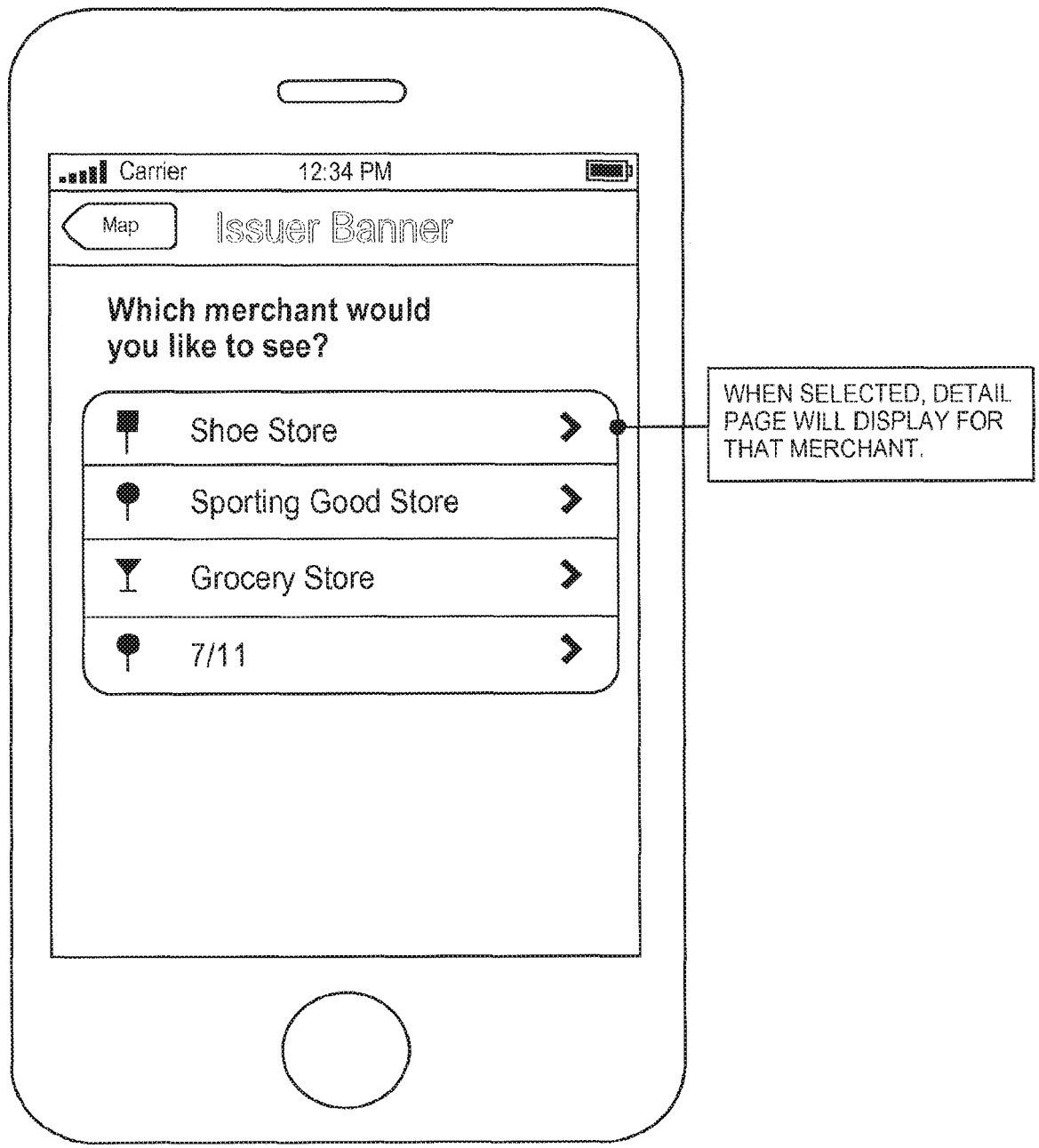

Alternately, if multiple contactless access devices corresponding to different merchants share the same geo-location, the application may display a menu querying which of the merchants the consumer would like to see. When a merchant is selected, merchant information for the selected merchant may be displayed as described above and illustrated in FIG. 20. An exemplary embodiment showing a merchant selection menu may be found in FIG. 22.

Figure 23:
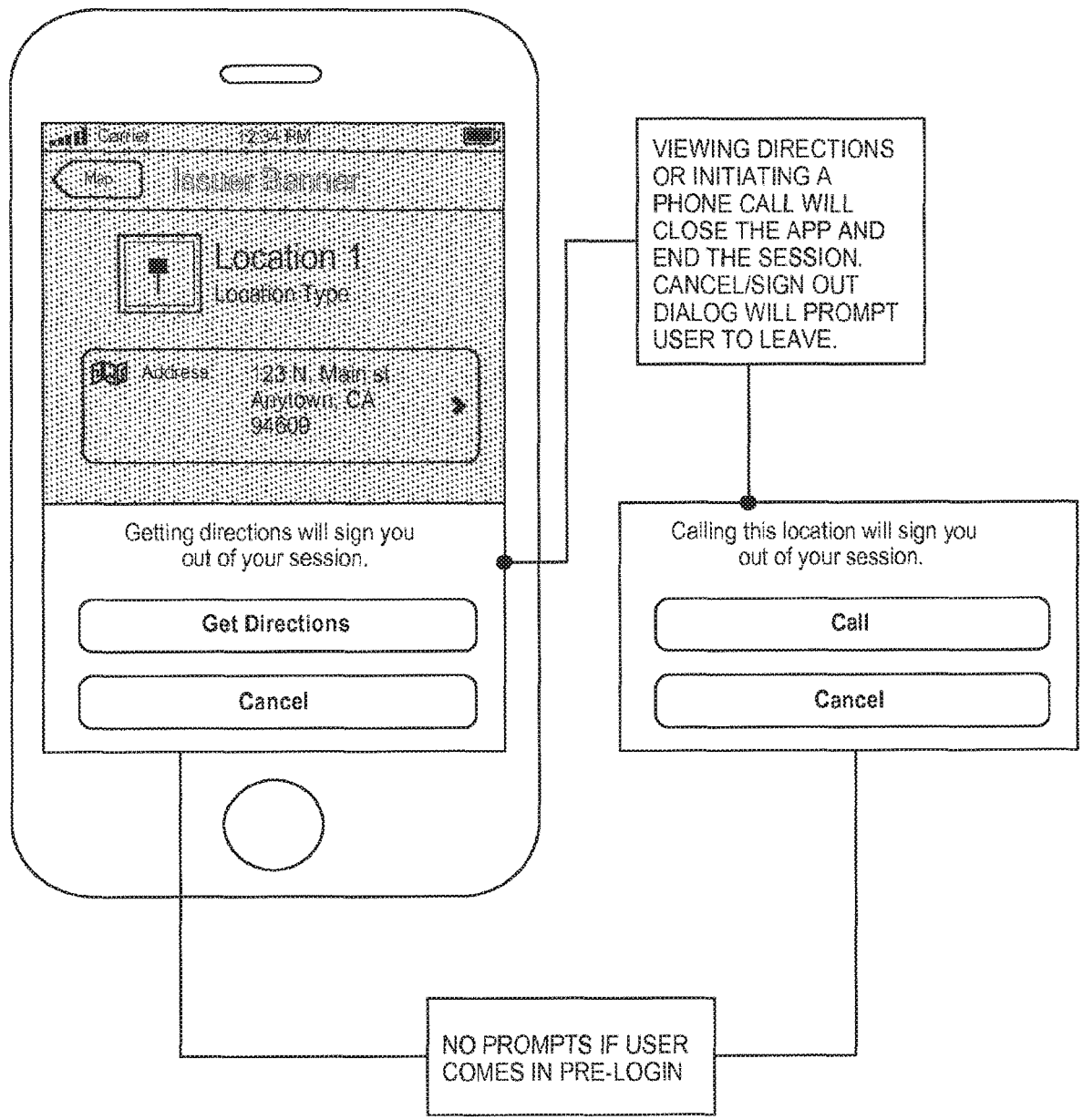

At step 908, the application performs an action based on a contactless access device based on input provided by the consumer. For example, the application may initiate a call, text, or email to a merchant associated with the contactless access device. Alternately, the application may generate directions to the geo-location of the contactless access device from the current consumer location. An exemplary screen prompting the consumer for an action is shown in FIG. 23.

VI. Exemplary Mapping Methods

Figure 24:
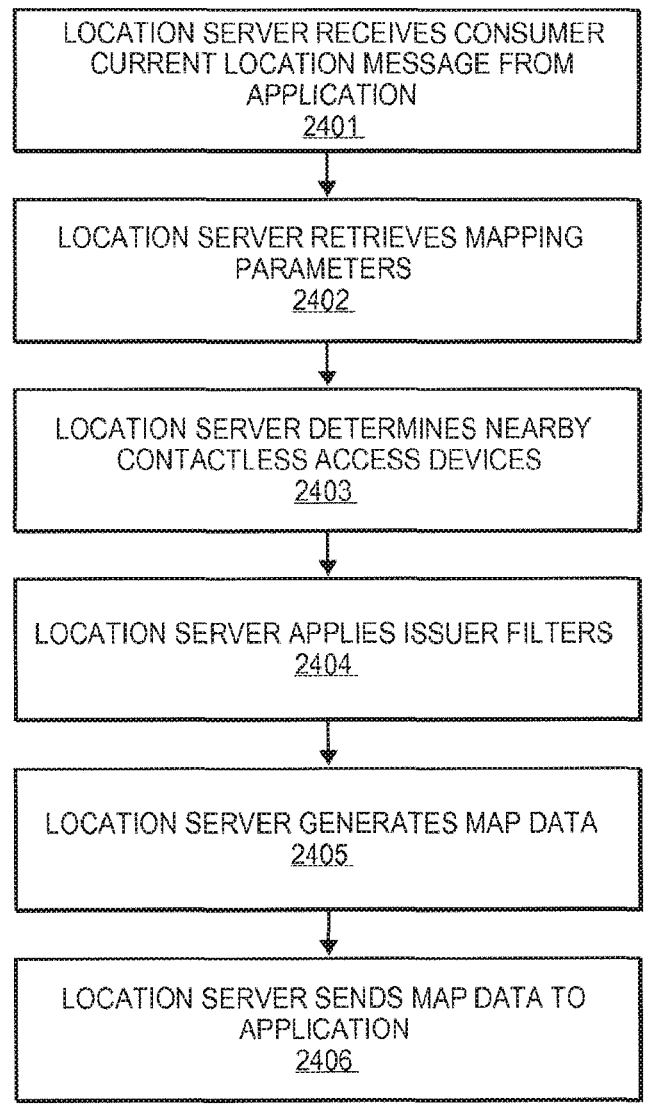
FIG. 24 illustrates a method for providing map data to an application.

FIG. 24 illustrates an exemplary method for providing map data to an application on a communications device 102, which can be provided by the location server computer 201 or other suitable computer. Typically, the flow is performed as a result of receiving a request from an application for map data.

At step 2401, the location server computer 201 electronically receives a consumer current location message from an application running on a communications device 102. The consumer current location may be expressed in any suitable form, such as a latitude-longitude pair, address, zip code, or city. In some embodiments of the invention, an issuer identifier for an issuer associated with the consumer may be included with the consumer current location message.

At step 2402, the location server retrieves the mapping parameters associated with the issuer 106 associated with the consumer 101. In some embodiments, as described above, an issuer identifier may be included in the consumer current location message. Alternatively, in various embodiments, an issuer identifier may be derived from consumer properties, such as the application used to electronically transmit the consumer current location message, or by cross referencing consumer information with databases stored by the payment processing network 200. The mapping parameters associated with the issuer 106 may be queried from the mapping database by using the issuer identifier.

At step 2403, the location server computer 201 determines nearby contactless access devices. The determination of whether a contactless access device is nearby may be made using one or more mapping parameters. For example, in some embodiments, an issuer 106 may define a contactless access device 112 as nearby if it lies within a certain distance of the current consumer location (e.g., within a 10-mile radius). In other embodiments, the issuer 106 may define the access device 112 as nearby if it is one of the closest contactless access devices (e.g., one of the 10 closest to the current consumer location). Once the criteria for nearby contactless access devices is determined, the location server computer 201 may query the location database 300 for the nearby contactless access devices.

At step 2404, the location server computer 201 applies any issuer filters defined in the mapping parameters. Issuer filters may be any filters on the location data which are intended to be applied for all consumers associated with the issuer, before map data is generated from the location data. In various embodiments of the invention, examples of issuer filters defined in the mapping database may include location type filters, merchant acquirer filters, contactless access device filters, or filters on any other location data stored for contactless access devices. Typically, a filter may specify a condition (such as a filter on the contactless technology used). If the condition is met by the contactless access device (if the technology used by the device is compatible), then the contactless access device may be included in generated map data. Otherwise, it may not be included in the generated map data.

At step 2405, the location server computer 201 generates map data corresponding to nearby contactless access devices which satisfy any issuer filters defined in the mapping parameters. Map data may also comprise properties of the contactless access devices, such as the make and model of the devices, and technologies supported by the devices. Map data may also comprise information regarding the a merchant, bank, ATM, or other institution associated with contactless access devices, such as addresses, phone numbers, customer ratings, hours of operation, and issuers and acquirers associated with the institutions. Typically, map data may be operable by an application to display a map, view information relating to contactless access devices, filter the contactless access devices, and perform actions based on the contactless access devices.

At step 2406, the location server computer 201 electronically transmits the map data to the application on the communications device 102.

Figure 25:
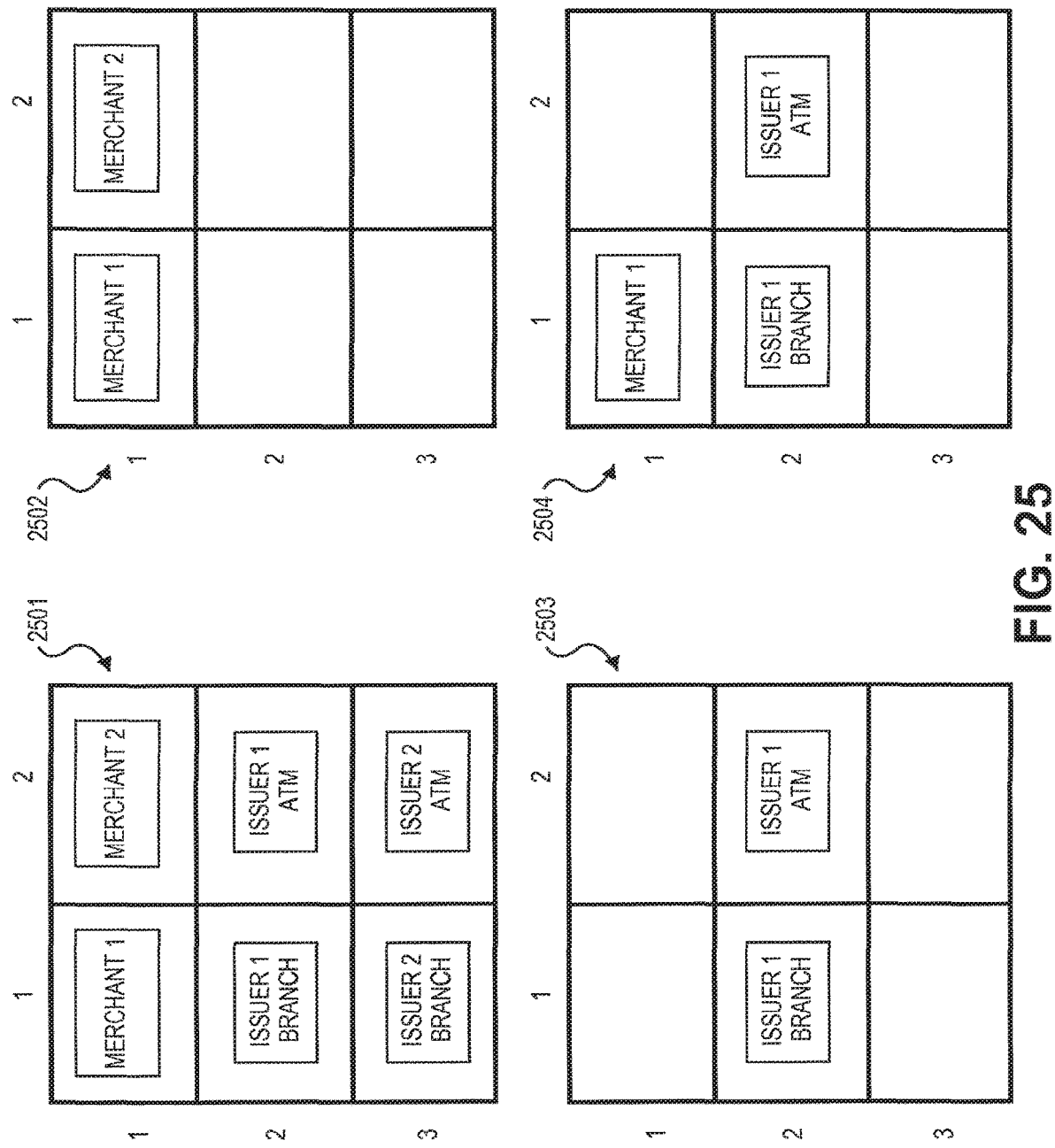
FIGS. 25-26 show schematic illustrations of the generated map data when filters are applied.
Figure 26:
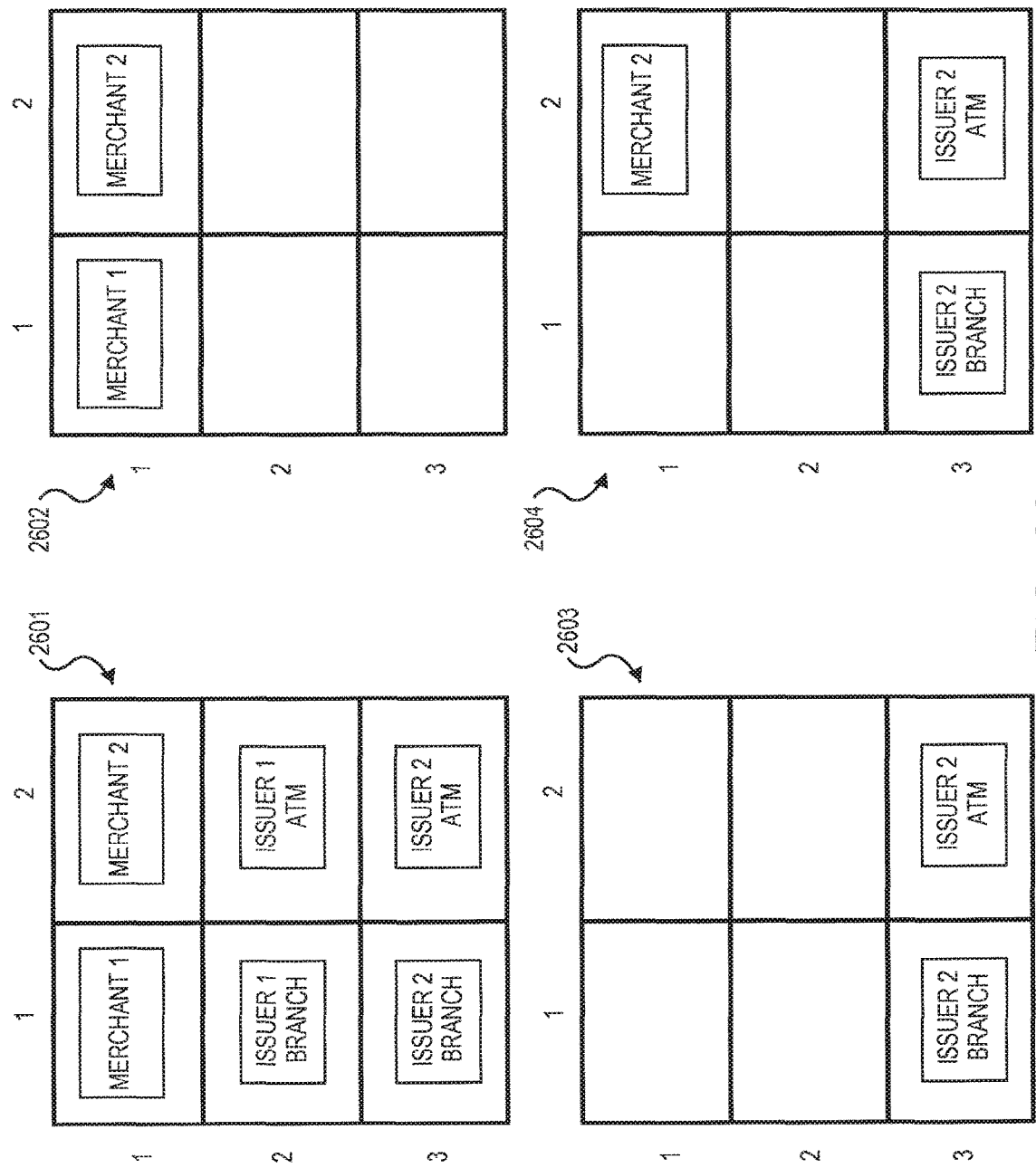

An exemplary illustration of the generated map data is shown in FIGS. 25 and 26. In particular, the grid 2501 represents the mapped geo-locations in a location database: Merchant 1 (grid location 1,1); Merchant 2 (grid location 1,2); Issuer 1 Branch (grid location 2,1); Issuer 1 ATM (grid location 2,2); Issuer 2 Branch (grid location 3,1); and Issuer 2 ATM (grid location 3,2), each comprising one or more contactless access devices.

The grid 2502 represents location data stored in a location database associated with merchants. In this case, location data associated with merchants may include information corresponding to Merchant 1 and Merchant 2, but may not include any bank branches or bank ATMs.

Grid 2503 may represent location data associated with Issuer 1: the location data corresponding to Issuer 1 Branch, and the location data corresponding to Issuer 1 ATM. Merchants 1 and 2 and Issuer 2 locations are not included In this example, Merchant 1 may provide an access device having a contactless interface that is compatible with the portable consumers devices provided by Issuer 1 (or Merchant 1 may provide other financial services related to Issuer 1, such as reloading pre-paid debit cards, etc.) and therefore Issuer 1 would like to provide this information to its customers in a customized map. Merchant 2 may not provide a similar functionality, and thereby Issuer 1 may not want to provide Merchant 2's location information to its consumers.

Therefore, with reference to grid 2504, Issuer 1 may define a filter in the mapping parameters to only display contactless access devices associated with Issuer 1 or merchants compatible with Issuer 1's technology. The resulting mapping is shown in grid 2504. Note that although the location database has location data for Merchant 2, because Issuer 1 may have indicated that it did not want to include non-compatible merchants in the custom mapping. The mapping represented by grid 2504 may then be provided by Issuer 1 to its customers (e.g., via a branded mobile application or web based platform).

FIG. 26 is similar to FIG. 25, except this illustrates the custom mapping for Issuer 2. In particular, the grid 2601 represents the location data stored in a location database. The grid 2602 represents the location data associated with merchants. However in this example, grid 2603 may represent location data associated with Issuer 2; that is, Issuer 2 may be associated with Issuer 2 Branch and Issuer 2 ATM, but it may not be associated with the Merchants or of Issuer 1.

In this example, Merchant 2 may provide an access device having a contactless interface that is compatible with the portable consumers devices provided by Issuer 2 (or Merchant 2 may provide other financial services related to Issuer 2, such as reloading pre-paid debit cards, etc.) and therefore Issuer 2 would like to provide this information to its customers in a customized map. Merchant 1 may not provide a similar functionality, and thereby Issuer 2 may not want to provide Merchant 1's location information to its consumers.

Therefore, with reference to grid 2604, Issuer 2 may define a filter in the mapping parameters to only display contactless access devices associated with Issuer 2 or merchants compatible with Issuer 2's technology. The resulting mapping is shown in grid 2604. Note that although the location database has location data for Merchant 1, because Issuer 2 indicated that it did not want to include non-compatible merchant access devices in the custom mapping, it was excluded. The mapping represented by grid 2604 may then be provided by Issuer 2 to its customers (e.g. via a branded mobile application or web based platform).

VII. Exemplary Consumer Devices, Access Devices, and Computer Apparatuses

Figure 27:
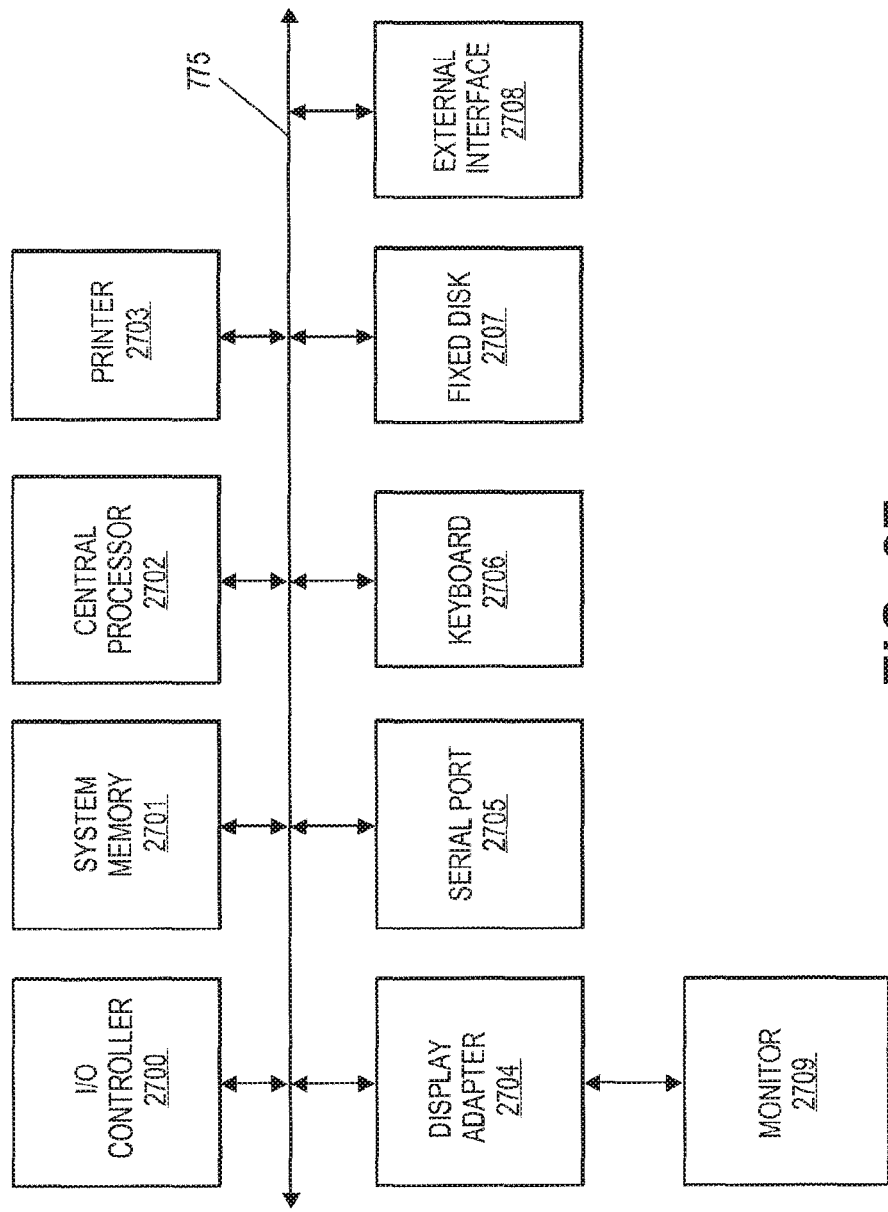
FIG. 27 shows a block diagram of components of an exemplary computer apparatus.

Referring now to FIG. 27, the various participants and elements in FIGS. 1-5 can operate one or more computer apparatuses (e.g., a server computer) to facilitate the functions described herein. Any of the elements in FIGS. 1-5 can use any suitable number of subsystems to facilitate the functions described herein. Examples of such subsystems or components are shown in FIG. 27. The subsystems shown in FIG. 27 are interconnected via a system bus 2710. Additional subsystems such as a printer 2703, keyboard 2706, fixed disk 2707 (or other memory comprising computer readable media), monitor 2709, which is coupled to display adapter 2704, and others are shown. Peripherals and input/output (I/O) devices, which coupled to I/O controller 2700, can be connected to the computer system by any number of means known in the art, such as serial port 2705. For example, serial port 2705 or external interface 2708 can be used to connect the computer apparatus to a wide area network such as the Internet, a mouse input device, or a scanner. The interconnection via system bus allows the central processor 2702 to communicate with each subsystem and to control the execution of instructions from system memory 2701 or the fixed disk 2707, as well as the exchange of information between subsystems. The system memory 2701 and/or the fixed disk 2707 can embody a computer readable medium.

Figure 28A:
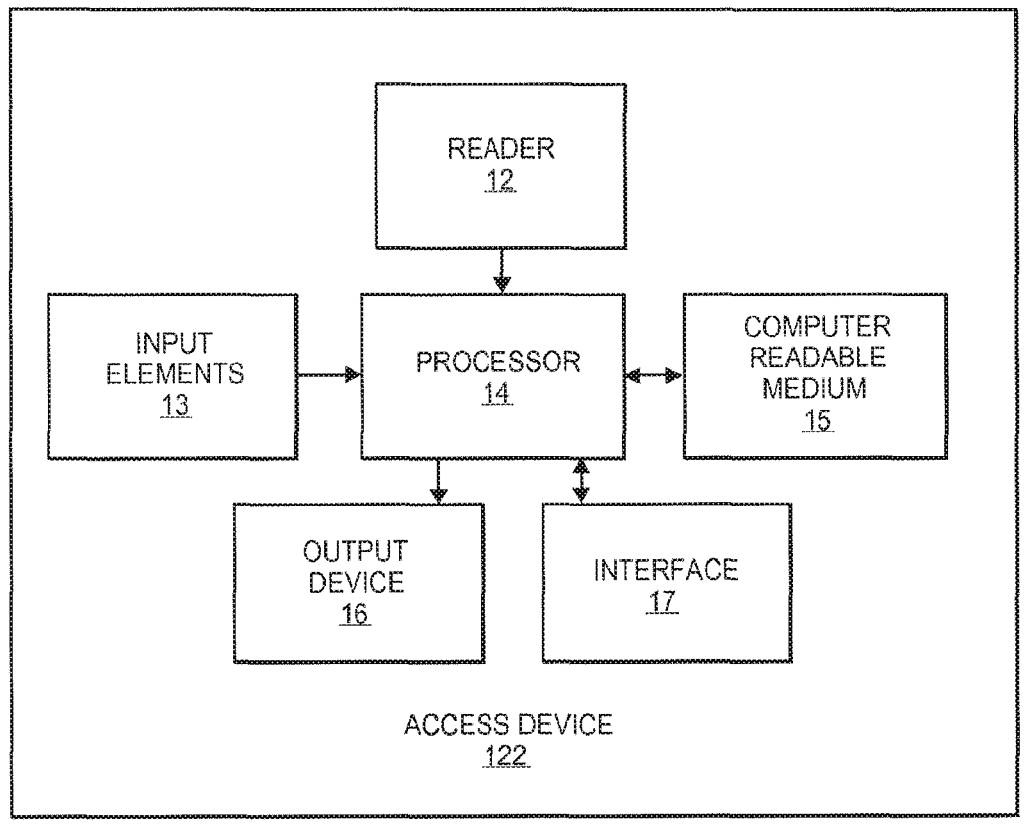
FIG. 28(a) shows block diagram of an access device.

Referring now to FIG. 28(a), a block diagram of access device 122, which can be a scanner, is illustrated according to an embodiment of the invention. Access device can be utilized interchangeably with access device or terminal, point of sale (POS) device or terminal, and/or reader and terminal within the present disclosure. The access device 122 comprises a processor 14 operatively coupled to a computer readable medium 15 (e.g., one or more memory chips, etc.), input elements 13 such as buttons or the like, one or more readers 12 (e.g., wireless short range communication interface (e.g., NFC), a barcode reader, optical scanner, etc.), an output device 16 (e.g., a display, a speaker, etc.) and an interface 17. A housing can contain one or more of these components. The computer readable medium 15 can comprise instructions or code, executable by a processor. The interface 17 can be a wired or wireless interface capable of communication with the merchant register. In another embodiment, interface 17 can be a network interface for direct communication with an acquirer, payment processing network, merchant computer apparatus, or any other device.

Figure 28B:
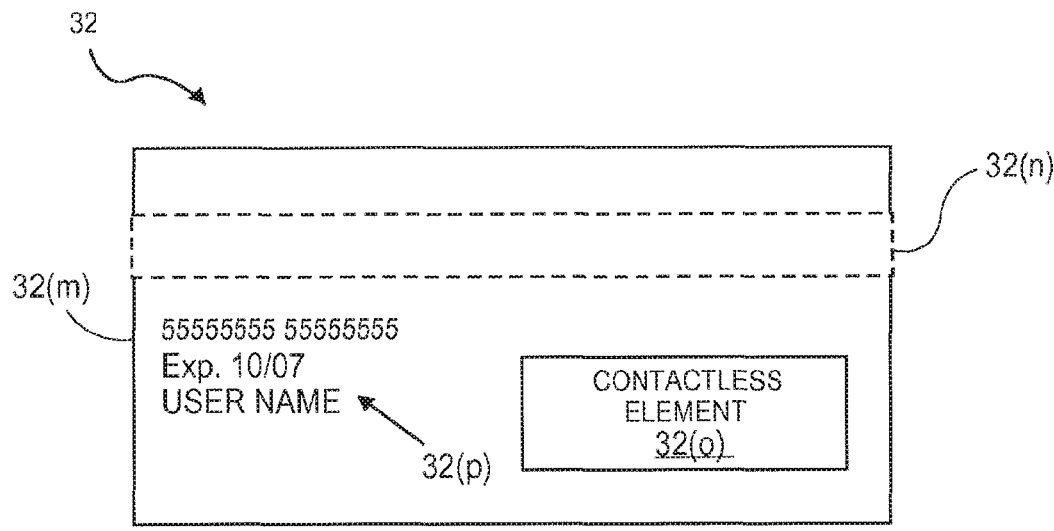
FIG. 28(b) shows a block diagram of an exemplary payment device.

As shown in FIG. 28(b), the payment device 32 may include both a magnetic stripe 32(n) and a contactless element 32(o). In other embodiments, both the magnetic stripe 32(n) and the contactless element 32(o) may be in the payment device 32. In other embodiments, either the magnetic stripe 32(n) or the contactless element 32(o) may be present in the payment device 32.

As described, the inventive service may involve implementing one or more functions, processes, operations or method steps. In some embodiments, the functions, processes, operations or method steps may be implemented as a result of the execution of a set of instructions or software code by a suitably-programmed computing device, microprocessor, data processor, or the like. The set of instructions or software code may be stored in a memory or other form of data storage element which is accessed by the computing device, microprocessor, etc. In other embodiments, the functions, processes, operations or method steps may be implemented by firmware or a dedicated processor, integrated circuit, etc.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions, or commands on a computer-readable medium, such as a random access memory (RAM), a read-only memory (ROM), a magnetic medium such as a hard-drive or a floppy disk, or an optical medium such as a CD-ROM. Any such computer-readable medium may reside on or within a single computational apparatus, and may be present on or within different computational apparatuses within a system or network.

While certain exemplary embodiments have been described in detail and shown in the accompanying drawings, it is to be understood that such embodiments are merely illustrative of and not intended to be restrictive of the broad invention, and that this invention is not to be limited to the specific arrangements and constructions shown and described, since various other modifications may occur to those with ordinary skill in the art.

As used herein, the use of "a", "an" or "the" is intended to mean "at least one", unless specifically indicated to the contrary.

What is claimed is:

1. A method comprising:
   electronically receiving, by a server computer, transaction data in an authorization request message from an access device for a transaction, wherein the transaction data is associated with a merchant and a transaction location, the access device being one of a plurality of access devices displayed via a map of a communication device, the plurality of access devices displayed via the map based on a filter;
   analyzing, by the server computer, the transaction data to determine if a location database comprises location data corresponding to the merchant associated with the transaction data; and
   adding, by the server computer, the transaction location and information regarding the access device to the location database.

2. The method of claim 1, further comprising determining if the transaction data indicates that the transaction was conducted using contactless payment, wherein adding the transaction location and information is further based on the determination that the transaction data indicates that the transaction was conducted using contactless payment.

3. The method of claim 1, wherein the authorization request message is received from the access device via an acquirer computer.

4. The method of claim 1, wherein the authorization request message comprises a transaction amount, and an access device identifier.

5. The method of claim 1, further comprising:
   determining, by the server computer, that an access device identifier for the access device is in the location database.

6. The method of claim 1, further comprising:
   determining, by the server computer, that an access device identifier for the access device is in the database;
   determining, by the server computer, that the transaction location is different than another transaction location in the location database that corresponds to the access device identifier.

7. The method of claim 1, wherein the transaction data comprises a contactless indicator flag.

8. The method of claim 1, wherein location data for the access device is in the transaction data.

9. The method of claim 8, wherein the location data comprises a latitude and longitude of the access device.

10. The method of claim 1, wherein the access device interacts with a contactless payment card prior to the receiving step.

11. A server computer comprising:
    a processor; and
    a computer readable medium, the computer readable medium comprising code, executable by the processor, for implementing a method comprising:
    receiving transaction data in an authorization request message from an access device for a transaction, wherein the transaction data is associated with a merchant and a transaction location, the access device being one of a plurality of access devices displayed via a map of a communications device, the plurality of access devices displayed via the map based on a filter;
    analyzing the transaction data to determine if a location database comprises location data corresponding to the merchant associated with the transaction data; and
    adding the transaction location and information regarding the access device to the location database.

12. The server computer of claim 11, further comprising determining if the transaction data indicates that the transaction was conducted using contactless payment, wherein adding the transaction location and information is further based on the determination that the transaction data indicates that the transaction was conducted using contactless payment.

13. The server computer of claim 11, wherein the authorization request message is received from the access device via an acquirer computer.

14. The server computer of claim 11, wherein the authorization request message comprises a transaction amount, and an access device identifier.

15. The server computer of claim 11, wherein the method further comprises:
    determining, by the server computer, that an access device identifier for the access device is in the location database.

16. The server computer of claim 11, wherein the method further comprises:
    determining, by the server computer, that an access device identifier for the access device is in the location database;
    determining, by the server computer, that the transaction location is different than another transaction location in the database that corresponds to the access device identifier.

17. The server computer of claim 11, wherein the transaction data comprises a contactless indicator flag.

18. The server computer of claim 11, wherein location data for the access device is in the transaction data.

19. The server computer of claim 11, wherein the location data comprises a latitude and longitude of the access device.

20. The server computer of claim 11, wherein the access device interacts with a contactless payment card prior to the receiving step.

* * * * *